US012653865B2

(12) United States Patent
Wu et al.

(10) Patent No.: US 12,653,865 B2
(45) Date of Patent: Jun. 16, 2026

(54) DUAL-AGONIST COMPOUND FOR BOTH GLP-1 AND GIP RECEPTORS AND APPLICATION THEREOF

(71) Applicant: Jiangsu Hengrui Pharmaceuticals Co., Ltd., Lianyungang (CN)

(72) Inventors: Fangzhou Wu, Beijing (CN); Lei Wang, Beijing (CN); Xuchao Huang, Beijing (CN); Ran Wu, Beijing (CN); Renzhi Liu, Beijing (CN); Haiqing Hua, Beijing (CN)

(73) Assignee: Jiangsu Hengrui Pharmaceuticals Co., Ltd., Lianyungang (CN)

( * ) Notice: Subject to any disclaimer, the term of this patent is extended or adjusted under 35 U.S.C. 154(b) by 698 days.

(21) Appl. No.: 17/927,304

(22) PCT Filed: May 28, 2021

(86) PCT No.: PCT/CN2021/096568
§ 371 (c)(1),
(2) Date: Nov. 22, 2022

(87) PCT Pub. No.: WO2021/239082
PCT Pub. Date: Dec. 2, 2021

(65) Prior Publication Data
US 2023/0190879 A1    Jun. 22, 2023

(30) Foreign Application Priority Data

May 29, 2020    (CN) ......................... 202010472577.8
Mar. 29, 2021    (CN) ......................... 202110335100.X

(51) Int. Cl.
*A61K 38/26*    (2006.01)
*A61P 3/04*    (2006.01)
*A61P 3/10*    (2006.01)
*C07K 14/605*    (2006.01)

(52) U.S. Cl.
CPC ............... *A61K 38/26* (2013.01); *A61P 3/04* (2018.01); *A61P 3/10* (2018.01); *C07K 14/605* (2013.01)

(58) Field of Classification Search
CPC ... A61K 38/26; A61P 3/04; A61P 3/10; C07K 14/605
See application file for complete search history.

(56) References Cited

U.S. PATENT DOCUMENTS

| | | |
|---|---|---|
| 10,370,426 B2 | 8/2019 | Oh et al. |
| 10,400,020 B2 | 9/2019 | Oh et al. |
| 2014/0011738 A1 | 1/2014 | DiMarchi |
| 2014/0018291 A1 | 1/2014 | Vignati et al. |
| 2014/0206608 A1 | 7/2014 | Haack et al. |
| 2014/0206609 A1 | 7/2014 | Haack et al. |
| 2017/0281788 A1 | 10/2017 | Dimarchi et al. |
| 2020/0024322 A1 | 1/2020 | Abraham et al. |
| 2022/0168396 A1 | 6/2022 | Wu et al. |
| 2024/0209056 A1 | 6/2024 | Yuan et al. |

FOREIGN PATENT DOCUMENTS

| | | |
|---|---|---|
| CN | 103764673 A | 4/2014 |
| CN | 104870009 A | 8/2015 |
| CN | 111825758 A | 10/2020 |
| CN | 115521368 A | 12/2022 |
| EP | 3954701 A1 | 2/2022 |
| JP | 2014-516994 A | 7/2014 |
| JP | 2015-521622 A | 7/2015 |
| JP | 2016-503770 A | 2/2016 |
| JP | 2016-503772 A | 2/2016 |
| JP | 2016-506401 A | 3/2016 |
| JP | 2017-534676 A | 11/2017 |
| JP | 2019-513126 A | 5/2019 |
| WO | WO-2006/097537 A2 | 9/2006 |
| WO | WO-2007/124461 A2 | 11/2007 |
| WO | 2011/080103 A1 | 7/2011 |
| WO | 2012/167744 A1 | 12/2012 |
| WO | 2014/091506 A1 | 6/2014 |
| WO | 2014/096145 A1 | 6/2014 |
| WO | WO-2014/096150 A1 | 6/2014 |
| WO | WO-2016/111971 A1 | 7/2016 |
| WO | WO-2016/131893 A1 | 8/2016 |
| WO | 2017/149070 A1 | 9/2017 |
| WO | WO-2018/237095 A1 | 12/2018 |
| WO | WO-2018/237097 A1 | 12/2018 |
| WO | WO-2019/193204 A1 | 10/2019 |
| WO | WO-2019/245893 A2 | 12/2019 |
| WO | WO-2020/023382 A1 | 1/2020 |

(Continued)

OTHER PUBLICATIONS

Jesper Lau et al., Discovery of the Once-Weekly Glucagon-Like Peptide-1 (GLP-1) Analogue Semaglutide, Journal of Medicinal Chemistry, Sep. 24, 2015, vol. 58, No. 18, pp. 7370-7380, Publication Date: Aug. 26, 2015 https://doi.org/10.1021/acs.jmedchem. 5b00726, Copyright © 2015 American Chemical Society (11 pages).

*Primary Examiner* — Gyan Chandra

(74) *Attorney, Agent, or Firm* — Choate, Hall & Stewart LLP; Charles E. Lyon; Michael A. Shinall

(57)    ABSTRACT

Provided is a dual-agonist compound for both Glucagon-like Peptide-1 (GLP-1) and Glucose-dependent Insulinotropic Polypeptide (GIP) receptors and application thereof. In particular, provided are a polypeptide analog derived from GLP-1 and a pharmaceutically acceptable salt thereof, which has an agonist effect on human GLP-1 receptor and human GIP receptor and can be used for the treatment of metabolic diseases such as obesity, type II diabetes, and non-alcoholic fatty liver.

38 Claims, 9 Drawing Sheets

Specification includes a Sequence Listing.

(56)         References Cited

FOREIGN PATENT DOCUMENTS

| | | |
|---|---|---|
| WO | WO-2020/023386 A1 | 1/2020 |
| WO | WO-2020/023388 A1 | 1/2020 |
| WO | WO-2020/067557 A2 | 4/2020 |
| WO | WO-2020/067575 A1 | 4/2020 |
| WO | 2020/207477 A1 | 10/2020 |
| WO | WO-2021/093883 A1 | 5/2021 |
| WO | WO-2021/113524 A2 | 6/2021 |
| WO | WO-2021/113535 A1 | 6/2021 |
| WO | WO-2021/193984 A2 | 9/2021 |
| WO | WO-2021/260530 A1 | 12/2021 |
| WO | WO-2022/018185 A1 | 1/2022 |
| WO | WO-2022/018186 A1 | 1/2022 |
| WO | WO-2022/079639 A1 | 4/2022 |
| WO | WO-2022/199629 A1 | 9/2022 |
| WO | WO-2022/257979 A1 | 12/2022 |
| WO | WO-2024/192219 A1 | 9/2024 |
| WO | WO-2025/024788 A1 | 1/2025 |

SEQUENCE LISTING

<160> NUMBER OF SEQ ID NOS: 20

<210> SEQ ID NO 1
<211> LENGTH: 39
<212> TYPE: PRT
<213> ORGANISM: artificial sequence
<220> FEATURE:
<223> OTHER INFORMATION: Synthetic Sequence
<220> FEATURE:
<221> NAME/KEY: misc_feature
<222> LOCATION: (2)..(2)
<223> OTHER INFORMATION: Xaa is Aib

<400> SEQUENCE: 1

Tyr Xaa Glu Gly Thr Phe Thr Ser Asp Tyr Ser Ile Tyr Lys Asp Lys
1               5                   10                  15

Ile Ala Ala Gln Glu Phe Val Asn Trp Leu Ile Ala Gly Gly Pro Ser
            20                  25                  30

Ser Gly Ala Pro Pro Pro Ser
        35

<210> SEQ ID NO 2
<211> LENGTH: 39
<212> TYPE: PRT
<213> ORGANISM: artificial sequence
<220> FEATURE:
<223> OTHER INFORMATION: Synthetic Sequence
<220> FEATURE:
<221> NAME/KEY: misc_feature
<222> LOCATION: (2)..(2)
<223> OTHER INFORMATION: Xaa is Aib

<400> SEQUENCE: 2

Tyr Xaa Glu Gly Thr Phe Thr Ser Asp Tyr Ser Ile Tyr Lys Asp Arg
1               5                   10                  15

Ile Ala Ala Gln Glu Phe Val Asn Trp Leu Ile Ala Gly Gly Pro Ser
            20                  25                  30

Ser Gly Ala Pro Pro Pro Ser
        35

<210> SEQ ID NO 3
<211> LENGTH: 39
<212> TYPE: PRT
<213> ORGANISM: artificial sequence
<220> FEATURE:
<223> OTHER INFORMATION: Synthetic Sequence
<220> FEATURE:
<221> NAME/KEY: misc_feature
<222> LOCATION: (2)..(2)
<223> OTHER INFORMATION: Xaa is Aib

<400> SEQUENCE: 3

Tyr Xaa Glu Gly Thr Phe Thr Ser Asp Tyr Ser Ile Tyr Lys Asp Lys
1               5                   10                  15

Ile Ala Ala Gln Glu Phe Ile Asn Trp Leu Ile Ala Gly Gly Pro Ser
            20                  25                  30

Ser Gly Ala Pro Pro Pro Ser
        35

<210> SEQ ID NO 4
<211> LENGTH: 39
<212> TYPE: PRT
<213> ORGANISM: artificial sequence
<220> FEATURE:
<223> OTHER INFORMATION: Synthetic Sequence
<220> FEATURE:

-continued

```
<221> NAME/KEY: misc_feature
<222> LOCATION: (2)..(2)
<223> OTHER INFORMATION: Xaa is Aib

<400> SEQUENCE: 4

Tyr Xaa Glu Gly Thr Phe Thr Ser Asp Tyr Ser Ile Tyr Lys Asp Arg
1               5                   10                  15

Ile Ala Ala Gln Glu Phe Ile Asn Trp Leu Ile Ala Gly Gly Pro Ser
            20                  25                  30

Ser Gly Ala Pro Pro Pro Ser
        35

<210> SEQ ID NO 5
<211> LENGTH: 39
<212> TYPE: PRT
<213> ORGANISM: artificial sequence
<220> FEATURE:
<223> OTHER INFORMATION: Synthetic Sequence
<220> FEATURE:
<221> NAME/KEY: misc_feature
<222> LOCATION: (2)..(2)
<223> OTHER INFORMATION: Xaa is Aib

<400> SEQUENCE: 5

Tyr Xaa Glu Gly Thr Phe Thr Ser Asp Tyr Ser Ile Tyr Lys Asp Lys
1               5                   10                  15

Ile Ala Ala Gln Glu Phe Ile Asn Trp Leu Leu Ala Gly Gly Pro Ser
            20                  25                  30

Ser Gly Ala Pro Pro Pro Ser
        35

<210> SEQ ID NO 6
<211> LENGTH: 39
<212> TYPE: PRT
<213> ORGANISM: artificial sequence
<220> FEATURE:
<223> OTHER INFORMATION: Synthetic Sequence
<220> FEATURE:
<221> NAME/KEY: misc_feature
<222> LOCATION: (2)..(2)
<223> OTHER INFORMATION: Xaa is Aib

<400> SEQUENCE: 6

Tyr Xaa Glu Gly Thr Phe Thr Ser Asp Tyr Ser Ile Tyr Lys Asp Arg
1               5                   10                  15

Ile Ala Ala Gln Glu Phe Val Asn Trp Leu Leu Ala Gly Gly Pro Ser
            20                  25                  30

Ser Gly Ala Pro Pro Pro Ser
        35

<210> SEQ ID NO 7
<211> LENGTH: 39
<212> TYPE: PRT
<213> ORGANISM: artificial sequence
<220> FEATURE:
<223> OTHER INFORMATION: Synthetic Sequence
<220> FEATURE:
<221> NAME/KEY: misc_feature
<222> LOCATION: (2)..(2)
<223> OTHER INFORMATION: Xaa is Aib

<400> SEQUENCE: 7

Tyr Xaa Glu Gly Thr Phe Thr Ser Asp Tyr Ser Ile Tyr Lys Asp Lys
1               5                   10                  15

Ile Ala Ala Gln Glu Phe Val Asn Trp Leu Leu Ala Gly Gly Pro Ser
```

-continued

```
            20              25              30

Ser Gly Ala Pro Pro Ser
        35

<210> SEQ ID NO 8
<211> LENGTH: 39
<212> TYPE: PRT
<213> ORGANISM: artificial sequence
<220> FEATURE:
<223> OTHER INFORMATION: Synthetic Sequence
<220> FEATURE:
<221> NAME/KEY: misc_feature
<222> LOCATION: (2)..(2)
<223> OTHER INFORMATION: Xaa is Aib

<400> SEQUENCE: 8

Tyr Xaa Glu Gly Thr Phe Thr Ser Asp Tyr Ser Ile Tyr Leu Glu Lys
1               5                   10                  15

Ile Ala Ala Gln Glu Phe Val Asn Trp Leu Leu Ala Gly Gly Pro Ser
            20                  25                  30

Ser Gly Ala Pro Pro Ser
        35

<210> SEQ ID NO 9
<211> LENGTH: 39
<212> TYPE: PRT
<213> ORGANISM: artificial sequence
<220> FEATURE:
<223> OTHER INFORMATION: Synthetic Sequence
<220> FEATURE:
<221> NAME/KEY: MISC_FEATURE
<222> LOCATION: (2)..(2)
<223> OTHER INFORMATION: Xaa is Aib

<400> SEQUENCE: 9

Tyr Xaa Glu Gly Thr Phe Thr Ser Asp Tyr Ser Ile Tyr Leu Glu Lys
1               5                   10                  15

Ile Ala Ala Gln Glu Phe Val Asn Trp Leu Ile Ala Gly Gly Pro Ser
            20                  25                  30

Ser Gly Ala Pro Pro Ser
        35

<210> SEQ ID NO 10
<211> LENGTH: 39
<212> TYPE: PRT
<213> ORGANISM: artificial sequence
<220> FEATURE:
<223> OTHER INFORMATION: Synthetic Sequence
<220> FEATURE:
<221> NAME/KEY: misc_feature
<222> LOCATION: (2)..(2)
<223> OTHER INFORMATION: Xaa is Aib

<400> SEQUENCE: 10

Tyr Xaa Glu Gly Thr Phe Thr Ser Asp Tyr Ser Ile Tyr Leu Glu Lys
1               5                   10                  15

Ile Ala Ala Gln Glu Phe Ile Asn Trp Leu Ile Ala Gly Gly Pro Ser
            20                  25                  30

Ser Gly Ala Pro Pro Ser
        35

<210> SEQ ID NO 11
<211> LENGTH: 39
<212> TYPE: PRT
<213> ORGANISM: artificial sequence
```

-continued

```
<220> FEATURE:
<223> OTHER INFORMATION: Synthetic Sequence
<220> FEATURE:
<221> NAME/KEY: misc_feature
<222> LOCATION: (2)..(2)
<223> OTHER INFORMATION: Xaa is Aib

<400> SEQUENCE: 11

Tyr Xaa Glu Gly Thr Phe Thr Ser Asp Tyr Ser Ile Tyr Leu Glu Lys
1               5                   10                  15

Ile Ala Ala Gln Glu Phe Ile Asn Trp Leu Leu Ala Gly Gly Pro Ser
            20                  25                  30

Ser Gly Ala Pro Pro Pro Ser
        35

<210> SEQ ID NO 12
<211> LENGTH: 39
<212> TYPE: PRT
<213> ORGANISM: artificial sequence
<220> FEATURE:
<223> OTHER INFORMATION: Synthetic Sequence
<220> FEATURE:
<221> NAME/KEY: misc_feature
<222> LOCATION: (2)..(2)
<223> OTHER INFORMATION: Xaa is Aib

<400> SEQUENCE: 12

Tyr Xaa Glu Gly Thr Phe Thr Ser Asp Tyr Ser Ile Tyr Lys Glu Lys
1               5                   10                  15

Ile Ala Ala Gln Glu Phe Val Asn Trp Leu Ile Ala Gly Gly Pro Ser
            20                  25                  30

Ser Gly Ala Pro Pro Pro Ser
        35

<210> SEQ ID NO 13
<211> LENGTH: 39
<212> TYPE: PRT
<213> ORGANISM: artificial sequence
<220> FEATURE:
<223> OTHER INFORMATION: Synthetic Sequence
<220> FEATURE:
<221> NAME/KEY: misc_feature
<222> LOCATION: (2)..(2)
<223> OTHER INFORMATION: Xaa is Aib

<400> SEQUENCE: 13

Tyr Xaa Glu Gly Thr Phe Thr Ser Asp Tyr Ser Ile Tyr Lys Glu Arg
1               5                   10                  15

Ile Ala Ala Gln Glu Phe Val Asn Trp Leu Ile Ala Gly Gly Pro Ser
            20                  25                  30

Ser Gly Ala Pro Pro Pro Ser
        35

<210> SEQ ID NO 14
<211> LENGTH: 39
<212> TYPE: PRT
<213> ORGANISM: artificial sequence
<220> FEATURE:
<223> OTHER INFORMATION: Synthetic Sequence
<220> FEATURE:
<221> NAME/KEY: misc_feature
<222> LOCATION: (2)..(2)
<223> OTHER INFORMATION: Xaa is Aib

<400> SEQUENCE: 14

Tyr Xaa Glu Gly Thr Phe Thr Ser Asp Tyr Ser Ile Tyr Lys Glu Lys
```

-continued

```
1               5               10              15

Ile Ala Ala Gln Glu Phe Ile Asn Trp Leu Ile Ala Gly Gly Pro Ser
            20              25              30

Ser Gly Ala Pro Pro Pro Ser
        35

<210> SEQ ID NO 15
<211> LENGTH: 39
<212> TYPE: PRT
<213> ORGANISM: artificial sequence
<220> FEATURE:
<223> OTHER INFORMATION: Synthetic Sequence
<220> FEATURE:
<221> NAME/KEY: misc_feature
<222> LOCATION: (2)..(2)
<223> OTHER INFORMATION: Xaa is Aib

<400> SEQUENCE: 15

Tyr Xaa Glu Gly Thr Phe Thr Ser Asp Tyr Ser Ile Tyr Lys Glu Arg
1               5               10              15

Ile Ala Ala Gln Glu Phe Ile Asn Trp Leu Ile Ala Gly Gly Pro Ser
            20              25              30

Ser Gly Ala Pro Pro Pro Ser
        35

<210> SEQ ID NO 16
<211> LENGTH: 39
<212> TYPE: PRT
<213> ORGANISM: artificial sequence
<220> FEATURE:
<223> OTHER INFORMATION: Synthetic Sequence
<220> FEATURE:
<221> NAME/KEY: misc_feature
<222> LOCATION: (2)..(2)
<223> OTHER INFORMATION: Xaa is Aib

<400> SEQUENCE: 16

Tyr Xaa Glu Gly Thr Phe Thr Ser Asp Tyr Ser Ile Tyr Lys Glu Lys
1               5               10              15

Ile Ala Ala Gln Glu Phe Ile Asn Trp Leu Leu Ala Gly Gly Pro Ser
            20              25              30

Ser Gly Ala Pro Pro Pro Ser
        35

<210> SEQ ID NO 17
<211> LENGTH: 39
<212> TYPE: PRT
<213> ORGANISM: artificial sequence
<220> FEATURE:
<223> OTHER INFORMATION: Synthetic Sequence
<220> FEATURE:
<221> NAME/KEY: MISC_FEATURE
<222> LOCATION: (2)..(2)
<223> OTHER INFORMATION: Xaa is Aib

<400> SEQUENCE: 17

Tyr Xaa Glu Gly Thr Phe Thr Ser Asp Tyr Ser Ile Tyr Lys Glu Arg
1               5               10              15

Ile Ala Ala Gln Glu Phe Val Asn Trp Leu Leu Ala Gly Gly Pro Ser
            20              25              30

Ser Gly Ala Pro Pro Pro Ser
        35

<210> SEQ ID NO 18
```

```
<211> LENGTH: 39
<212> TYPE: PRT
<213> ORGANISM: artificial sequence
<220> FEATURE:
<223> OTHER INFORMATION: Synthetic Sequence
<220> FEATURE:
<221> NAME/KEY: MISC_FEATURE
<222> LOCATION: (2)..(2)
<223> OTHER INFORMATION: Xaa is Aib

<400> SEQUENCE: 18

Tyr Xaa Glu Gly Thr Phe Thr Ser Asp Tyr Ser Ile Tyr Lys Glu Lys
1               5                   10                  15

Ile Ala Ala Gln Glu Phe Val Asn Trp Leu Leu Ala Gly Gly Pro Ser
            20                  25                  30

Ser Gly Ala Pro Pro Pro Ser
        35

<210> SEQ ID NO 19
<211> LENGTH: 39
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is selected from the group consisting of
     amino acid residues of Tyr and His
<220> FEATURE:
<221> NAME/KEY: misc_feature
<222> LOCATION: (2)..(2)
<223> OTHER INFORMATION: Xaa is selected from the group consisting of
     amino acid residues of Aib and D-Ala
<220> FEATURE:
<221> NAME/KEY: misc_feature
<222> LOCATION: (10)..(10)
<223> OTHER INFORMATION: Xaa is selected from the group consisting of
     amino acid residues of Val and Tyr
<220> FEATURE:
<221> NAME/KEY: misc_feature
<222> LOCATION: (12)..(12)
<223> OTHER INFORMATION: Xaa is selected from the group consisting of
     amino acid residues of Ser and Ile
<220> FEATURE:
<221> NAME/KEY: misc_feature
<222> LOCATION: (13)..(13)
<223> OTHER INFORMATION: Xaa is selected from the group consisting of
     amino acid residues of Tyr and Ala
<220> FEATURE:
<221> NAME/KEY: misc_feature
<222> LOCATION: (14)..(14)
<223> OTHER INFORMATION: Xaa is selected from the group consisting of
     amino acid residues of Leu and Nle
<220> FEATURE:
<221> NAME/KEY: misc_feature
<222> LOCATION: (15)..(15)
<223> OTHER INFORMATION: Xaa is selected from the group consisting of
     amino acid residues of Asp and Glu
<220> FEATURE:
<221> NAME/KEY: misc_feature
<222> LOCATION: (16)..(16)
<223> OTHER INFORMATION: Xaa is selected from the group consisting of
     amino acid residues of Arg, Glu, Gly, Lys and Aib
<220> FEATURE:
<221> NAME/KEY: misc_feature
<222> LOCATION: (17)..(17)
<223> OTHER INFORMATION: Xaa is selected from the group consisting of
     amino acid residues of Glu, Ile and Gln
<220> FEATURE:
<221> NAME/KEY: misc_feature
<222> LOCATION: (18)..(18)
<223> OTHER INFORMATION: Xaa is selected from the group consisting of
     amino acid residues of Ala, Aib and His
<220> FEATURE:
```

```
<221> NAME/KEY: misc_feature
<222> LOCATION: (19)..(19)
<223> OTHER INFORMATION: Xaa is selected from the group consisting of
      amino acid residues of Ala, Aib and Gln
<220> FEATURE:
<221> NAME/KEY: misc_feature
<222> LOCATION: (20)..(20)
<223> OTHER INFORMATION: Xaa is selected from the group consisting of
      amino acid residues of Gln, Glu and Lys
<220> FEATURE:
<221> NAME/KEY: misc_feature
<222> LOCATION: (23)..(23)
<223> OTHER INFORMATION: Xaa is selected from the group consisting of
      amino acid residues of Ile and Val
<220> FEATURE:
<221> NAME/KEY: misc_feature
<222> LOCATION: (24)..(24)
<223> OTHER INFORMATION: Xaa is selected from the group consisting of
      amino acid residues of Ala, Asn and Gln
<220> FEATURE:
<221> NAME/KEY: misc_feature
<222> LOCATION: (27)..(27)
<223> OTHER INFORMATION: Xaa is selected from the group consisting of
      amino acid residues of Val and Leu
<220> FEATURE:
<221> NAME/KEY: misc_feature
<222> LOCATION: (28)..(28)
<223> OTHER INFORMATION: Xaa is selected from the group consisting of
      amino acid residues of Arg and Ala
<220> FEATURE:
<221> NAME/KEY: misc_feature
<222> LOCATION: (29)..(29)
<223> OTHER INFORMATION: Xaa is selected from the group consisting of
      amino acid residues of Gly and Gln
<220> FEATURE:
<221> NAME/KEY: misc_feature
<222> LOCATION: (30)..(30)
<223> OTHER INFORMATION: Xaa is selected from the group consisting of
      amino acid residues of Gly and Lys

<400> SEQUENCE: 19

Xaa Xaa Glu Gly Thr Phe Thr Ser Asp Xaa Ser Xaa Xaa Xaa Xaa Xaa
1               5                   10                  15

Xaa Xaa Xaa Xaa Glu Phe Xaa Xaa Trp Leu Xaa Xaa Xaa Xaa Pro Ser
            20                  25                  30

Ser Gly Ala Pro Pro Pro Ser
        35

<210> SEQ ID NO 20
<211> LENGTH: 39
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (2)..(2)
<223> OTHER INFORMATION: Xaa is Aib
<220> FEATURE:
<221> NAME/KEY: misc_feature
<222> LOCATION: (14)..(14)
<223> OTHER INFORMATION: Xaa is Lys or Leu
<220> FEATURE:
<221> NAME/KEY: misc_feature
<222> LOCATION: (15)..(15)
<223> OTHER INFORMATION: Xaa is Asp or Glu
<220> FEATURE:
<221> NAME/KEY: misc_feature
<222> LOCATION: (16)..(16)
<223> OTHER INFORMATION: Xaa is Lys or Arg
<220> FEATURE:
<221> NAME/KEY: misc_feature
<222> LOCATION: (23)..(23)
<223> OTHER INFORMATION: Xaa is Val or Ile
<220> FEATURE:
```

-continued

```
<221> NAME/KEY: misc_feature
<222> LOCATION: (27)..(27)
<223> OTHER INFORMATION: Xaa is Ile or Leu

<400> SEQUENCE: 20

Tyr Xaa Glu Gly Thr Phe Thr Ser Asp Tyr Ser Ile Tyr Xaa Xaa Xaa
1               5                   10                  15

Ile Ala Ala Gln Glu Phe Xaa Asn Trp Leu Xaa Ala Gly Gly Pro Ser
            20                  25                  30

Ser Gly Ala Pro Pro Pro Ser
        35
```

DUAL-AGONIST COMPOUND FOR BOTH GLP-1 AND GIP RECEPTORS AND APPLICATION THEREOF

CROSS-REFERENCE TO RELATED APPLICATIONS

The present application is a national stage application of International Patent Application No. PCT/CN2021/096568, filed May 28, 2021, which claims the benefit of and priority to Chinese Patent Application No. 202010472577.8 filed on May 29, 2020 and Chinese Patent Application No. 202110335100.X filed on Mar. 29, 2021, all of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Oct. 12, 2022, is named "721055CPUS_126268-5045-US_ST25 Sequence Listing. TXT" and is approximately 12 kilobytes in size.

TECHNICAL FIELD

The present disclosure relates to the field of biological pharmaceutics, in particular to a compound and a pharmaceutically acceptable salt thereof having a dual-agonist effect on a human glucagon-like peptide-1 (GLP-1) receptor and a human glucose-dependent insulinotropic polypeptide (GIP) receptor, which can be used for the treatment of metabolic diseases such as diabetes and/or obesity.

BACKGROUND

Diabetes is a metabolic disease in which the metabolism of glucose, protein and lipid in a human body is disordered due to insufficient insulin secretion in the body. Diabetes is mainly classified into insulin-dependent diabetes (type I diabetes) and non-insulin-dependent diabetes (type II diabetes) according to the differences in its pathological mechanisms. Among them, 90%-95% of diabetic patients worldwide are non-insulin-dependent diabetic patients. Non-insulin-dependent diabetes is a long-term chronic metabolic disease caused by impaired pancreatic β cell function and long-term insulin resistance, which is primarily characterized by a deficiency in the insulin level in the body and high blood glucose concentrations in the plasma. Studies have shown that non-insulin-dependent diabetes is associated with a variety of high risk complications in patients and can often lead to patients suffering from cardiovascular disease, kidney failure, blindness, amputation, and a variety of other complications.

One of the major causes of non-insulin-dependent diabetes is obesity. Obesity is defined as an excessive or abnormal accumulation of fat in the body that is detrimental to one's health. Obesity can also be defined as the case where the body mass index (BMI) of a person is greater than or equal to 30 kg/m² according to the person's BMI. The rise of obesity can significantly increase the risk of cardiovascular disease, diabetes, musculoskeletal disorders and certain cancers in humans. In addition, an increase in a person's body mass index also increases the risk of certain non-infectious diseases.

Due of the huge number of patients and the significant economic burden caused by diabetes and its complications, the development of safe and effective drugs for the treatment of diabetes has always been one of the focus areas of attention of many research institutes and pharmaceutical enterprises. At present, the diabetes drugs approved on the market mainly include chemically synthesized small-molecule oral hypoglycemic drugs such as biguanides, sulfonamides, insulin sensitizers and α-glucosides, and biologically synthesized injectable hypoglycemic drugs such as recombinant insulin and its derivatives. Although the above drugs are clinically effective in controlling the blood glucose level in plasma of diabetic patients, their long-term use is often accompanied by adverse reactions such as weight gain of patients, which in turn leads to an increased risk of potential cardiovascular disease and reduced compliance of use of patients. Considering the potential pathological relationship between diabetes and obesity and the potential risk of complications caused by obesity, the development of a drug that can not only effectively control blood glucose but also appropriately reduce the weight of diabetic patients has multiple meanings for the effective treatment of diabetes and the reduction of the potential risk of complications, and is therefore a better direction for clinical development.

Glucagon-like peptide-1 (GLP-1) is a gastrointestinal regulatory peptide containing 30 or 31 amino acid residues. The secretion of GLP-1 is mainly regulated by L-cells of the small intestine in response to nutrient absorption and fluctuating blood glucose level in vivo. After food intake, L-cells of the small intestine secrete large amounts of GLP-1 to enhance the endocrine function of the pancreas. GLP-1 polypeptide performs its physiological functions of controlling blood glucose and reducing appetite in vivo mainly by activating GLP-1 receptors distributed on the surface of cell membrane. The mechanism of GLP-1 for controlling the blood glucose level in vivo is mainly to activate GLP-1 receptors distributed in pancreatic β cells so as to promote biosynthesis and secretion of insulin. Meanwhile, GLP-1 polypeptide can inhibit glucagon secretion, gastric emptying and food intake in the presence of high blood glucose level in the body, and enhance the degradation of glucose in the body through specific neurological actions. Notably, the physiological function of GLP-1 polypeptide to promote insulin secretion is controlled by the concentration of plasma glucose, so that GLP-1 polypeptide does not cause severe and long-lasting hypoglycemia compared to other diabetes treatment drugs. In addition, it has been reported in the literature that GLP-1 polypeptide and analogs thereof have direct promotion effects on the growth, differentiation and proliferation of β cells of experimental animals, indicating that GLP-1 polypeptide and analogs thereof can protect pancreatic islets, delay the progression of diabetes and inhibit the apoptosis of β cells. GLP-1 polypeptide also has a potential effect on inhibiting the secretion of gastrin and feeding-stimulated gastric acid. Those characteristics imply that GLP-1 polypeptide also has a physiological effect of preventing peptic ulcers. GLP-1 polypeptide can also activate GLP-1 receptors distributed in the central nervous system of the brain to enhance satiety, reduce food intake, and achieve the physiological effect of maintaining or reducing body weight. Therefore, the extensive mechanisms of action and physiological functions of GLP-1 polypeptide and analogs thereof imply that GLP-1 polypeptide is an ideal medicament for the treatment of non-insulin-dependent diabetes and obesity diabetes.

The physiological functions of GLP-1 polypeptide such as controlling blood glucose and reducing body weight hold promise for the treatment of non-insulin-dependent diabetes/obesity diabetes. Natural GLP-1 has poor druggability and is readily degraded by dipeptidyl peptidase-IV (DPP-IV) in vivo, and thus has a half-life of only 1-2 min in humans. In the face of this difficulty, the pharmaceutical industry has constructed long-acting GLP-1 analogs and derivatives thereof by site-directed mutagenesis of amino acids at the enzymatic digestion site, fatty acid modification of the polypeptide skeleton, and coupling of GLP-1 polypeptide to a variety of protein/polymer polymers. Long-acting GLP-1 analogs that are currently on the market and are widely used clinically include liraglutide (subcutaneous injection once a day) and dulaglutide and semaglutide (subcutaneous injection once a week).

Clinically, the side effects of GLP-1 polypeptide and derivatives thereof mainly include nausea, vomiting and diarrhea induced by the gastrointestinal tract. In addition, it has been found that GLP-1 polypeptide and derivatives thereof can also trigger tachycardia in subjects and, in certain cases, increase the risk of pancreatitis in patients. Therefore, the dosage of GLP-1 polypeptide and derivatives thereof is limited by the side effects they cause, so that their clinical use cannot achieve full-effect blood glucose control and weight loss in patients.

Glucose-dependent insulinotropic polypeptide (GIP) and GLP-1 polypeptide are both incretins, which play a key physiologically related role in the metabolism of blood glucose in the body. GIP is mainly composed of 42 amino acid residues in the body and is secreted by K cells in duodenum and adjacent jejunum in response to the glucose level in plasma. GIP polypeptides exert their physiological effects by binding to GIP receptors distributed in the pancreatic β cells, adipose tissue and central nervous system. Similar to GLP-1 polypeptide, GIP polypeptide can stimulate the secretion of insulin from pancreatic β cells, thereby reducing the concentration of blood glucose in the plasma, and can protect pancreatic β cells, thereby controlling the metabolism of glucose in the body. In addition, the physiological functions of GIP polypeptide further include activation of GIP receptors in adipose tissue, thereby promoting the metabolism of fat. Intraventricular injection of GIP polypeptide in mice can reduce food intake and body weight of the test animals, which seems to suggest that GIP polypeptide also has a physiological function in reducing body weight. Studies have shown that in non-insulin-dependent diabetic patients, the incretin function of GIP polypeptide is greatly reduced, resulting in a lack or loss of incretin effect in the patients. Studies have shown that the inhibitory properties of the GIP polypeptide produced by those diabetic patients are greatly diminished when the blood glucose level returns to normal.

Therefore, there is a clinical need for a method for treating non-insulin-dependent diabetes using the GIP polypeptide in combination with a clinically effective hypoglycemic drug to restore the tolerance of the non-insulin-dependent diabetic patients to the GIP polypeptide, and further in combination with the incretin effect of the GIP polypeptide to obtain a stronger clinical hypoglycemic effect.

The present disclosure aims to provide a derivative of a GLP-1 analog having agonist activity to a human GIP receptor, which has a dual-agonist effect on the human GLP-1 receptor and the human GIP receptor. In addition, some of the compounds of the present disclosure have greater efficacy in lowering blood glucose and reducing body weight compared to GLP-1 receptor agonists known in the art. Some of the compounds of the present disclosure have extremely high plasma stability and have pharmacokinetic characteristics for subcutaneous injection once a week in human subjects.

4

SUMMARY

The present disclosure provides a GLP-1 analog having general formula (I) or a pharmaceutically acceptable salt thereof:

(I)
(SEQ ID NO: 19)
R$_1$-X$_1$-X$_2$-Glu-Gly-Thr-Phe-Thr-Ser-Asp-

X$_{10}$-Ser-X$_{12}$-X$_{13}$-X$_{14}$-X$_{15}$-X$_{16}$-X$_{17}$-X$_{18}$-X$_{19}$-

X$_{20}$-Glu-Phe-X$_{23}$-X$_{24}$-Trp-Leu-X$_{27}$-X$_{28}$-X$_{29}$-

X$_{30}$-Pro-Ser-Ser-Gly-Ala-Pro-Pro-Pro-

Ser-R$_2$ wherein:
R$_1$ is hydrogen (H), alkyl, acetyl, formyl, benzoyl, trifluoroacetyl, pGlu or absent;
R$_2$ is —NH$_2$, —OH or absent;
X$_1$, X$_2$, X$_{10}$, X$_{12}$, X$_{13}$, X$_{14}$, X$_{15}$, X$_{16}$, X$_{17}$, X$_{18}$, X$_{19}$, X$_{20}$, X$_{23}$, X$_{24}$, X$_{27}$, X$_{28}$, X$_{29}$ and X$_{30}$ are independently selected from the group consisting of any natural amino acid residues, any non-natural amino acid residues, and peptide fragments composed of natural amino acid residues and/or non-natural amino acid residues.

Some embodiments of the present disclosure provide a GLP-1 analog having general formula (I) or a pharmaceutically acceptable salt thereof, wherein X$_1$ is selected from the group consisting of amino acid residues of Tyr and His; X$_2$ is selected from the group consisting of amino acid residues of Aib and D-Ala; X$_{10}$ is selected from the group consisting of amino acid residues of Val and Tyr; X$_{12}$ is selected from the group consisting of amino acid residues of Ser and Ile; X$_{13}$ is selected from the group consisting of amino acid residues of Tyr and Ala; X$_{14}$ is selected from the group consisting of amino acid residues of Leu and Nle; X$_{15}$ is selected from the group consisting of amino acid residues of Asp and Glu; X$_{16}$ is selected from the group consisting of amino acid residues of Arg, Glu, Gly, Lys and Aib; X$_{17}$ is selected from the group consisting of amino acid residues of Glu, Ile and Gln; X$_{18}$ is selected from the group consisting of amino acid residues of Ala, Aib and His; X$_{19}$ is selected from the group consisting of amino acid residues of Ala, Aib and Gln; X$_{20}$ is selected from the group consisting of amino acid residues of Gln, Glu and Lys; X$_{23}$ is selected from the group consisting of amino acid residues of Ile and Val; X$_{24}$ is selected from the group consisting of amino acid residues of Ala, Asn and Gln; X$_{27}$ is selected from the group consisting of amino acid residues of Val and Leu; X$_{28}$ is selected from the group consisting of amino acid residues of Arg and Ala; X$_{29}$ is selected from the group consisting of amino acid residues of Gly and Gln; and X$_{30}$ is selected from the group consisting of amino acid residues of Gly and Lys.

Some embodiments of the present disclosure provide a GLP-1 analog having general formula (I) or a pharmaceutically acceptable salt thereof, wherein X$_1$ is selected from the group consisting of amino acid residues of Tyr and His; X$_2$ is selected from the group consisting of amino acid residues of Aib and D-Ala; X$_{10}$ is selected from the group consisting of amino acid residues of Val and Tyr and Y1; X$_{12}$ is selected from the group consisting of amino acid residues of Ser and Ile and Y1; X$_{13}$ is selected from the group consisting of amino acid residues of Tyr and Ala and Y1; X$_{14}$ is selected from the group consisting of amino acid residues of Leu and Nle and Y1; X$_{15}$ is selected from the group consisting of amino acid residues of Asp and Glu; $X_{16}$ is selected from the group consisting of amino acid residues of Arg, Glu, Gly, Lys and Aib and Y1; $X_{17}$ is selected from the group consisting of amino acid residues of Glu, Ile and Gln and Y1; $X_{18}$ is selected from the group consisting of amino acid residues of Ala, Aib and His; $X_{19}$ is selected from the group consisting of amino acid residues of Ala, Aib and Gln; $X_{20}$ is selected from the group consisting of amino acid residues of Gln, Glu and Lys; $X_{23}$ is selected from the group consisting of amino acid residues of Ile and Val; $X_{24}$ is selected from the group consisting of amino acid residues of Ala, Asn and Gln; $X_{27}$ is selected from the group consisting of amino acid residues of Val and Leu; $X_{28}$ is selected from the group consisting of amino acid residues of Arg and Ala; $X_{29}$ is selected from the group consisting of amino acid residues of Gly and Gln; and $X_{30}$ is selected from the group consisting of amino acid residues of Gly and Lys; Y1 is a substituted Lys, Orn, Dap, Dab or Cys residue, specifically with a modified group on a side chain of the Lys, Orn, Dap, Dab or Cys residue. In some embodiments, Y1 is a Lys, Orn, Dap, Dab or Cys residue with a substituent on a side chain, the substituent having a structure of formula {[2-(2-amino-ethoxy)-ethoxy]-acetyl}$_a$-(y-Glu)$_b$-CO—(CH$_2$)$_c$—COOH; wherein: a is an integer of 1-3 (reference may be made to 1, 2 or 3); b is 1 or 2; c is an integer of 10-30 (reference may be made to 10, 11, 12, 13, 14, 15, 16, 17, 18, 19, 20, 21, 22, 23, 24, 25, 26, 27, 28, 29 or 30).

Some embodiments of the present disclosure provide a GLP-1 analog having general formula (I) or a pharmaceutically acceptable salt thereof, wherein $X_1$ is selected from an amino acid residue of Tyr; $X_2$ is selected from an amino acid residue of Aib; $X_{10}$ is selected from an amino acid residue of Tyr; $X_{12}$ is selected from an amino acid residue of Ile; $X_{13}$ is selected from an amino acid residue of Tyr; $X_{14}$ is selected from Y1; $X_{18}$ is selected from the group consisting of amino acid residues of Asp and Glu; $X_{16}$ is selected from the group consisting of amino acid residues of Arg and Lys; $X_{17}$ is selected from an amino acid residue of Ile; $X_{18}$ is selected from an amino acid residue of Ala; $X_{19}$ is selected from an amino acid residue of Ala; $X_{20}$ is selected from an amino acid residue of Gln; $X_{23}$ is selected from the group consisting of amino acid residues of Ile and Val; $X_{24}$ is selected from an amino acid residue of Asn; $X_{27}$ is selected from the group consisting of amino acid residues of Ile and Leu; $X_{28}$ is selected from an amino acid residue of Ala; $X_{29}$ is selected from an amino acid residue of Gly; $X_{30}$ is selected from an amino acid residue of Gly; Y1 is a Lys, Orn, Dap, Dab or Cys residue with the side chain connected to a substituent of formula {[2-(2-amino-ethoxy)-ethoxy]-acetyl}$_a$-(y-Glu)$_b$-CO—(CH$_2$)$_c$—COOH; a is an integer of 1-3; b is 1 or 2; c is an integer of 10-30.

Some embodiments of the present disclosure provide a GLP-1 analog having general formula (I) or a pharmaceutically acceptable salt thereof, wherein $X_1$ is selected from an amino acid residue of Tyr; $X_2$ is selected from an amino acid residue of Aib; $X_{10}$ is selected from an amino acid residue of Tyr; $X_{12}$ is selected from an amino acid residue of Ile; $X_{13}$ is selected from an amino acid residue of Tyr; $X_{14}$ is selected from Y1; $X_{15}$ is selected from the group consisting of amino acid residues of Asp and Glu; $X_{16}$ is selected from an amino acid residue of Lys; $X_{17}$ is selected from an amino acid residue of Ile; $X_{18}$ is selected from an amino acid residue of Ala; $X_{19}$ is selected from an amino acid residue of Ala; $X_{20}$ is selected from an amino acid residue of Gln; $X_{23}$ is selected from an amino acid residue of Val; $X_{24}$ is selected from an amino acid residue of Asn; $X_{27}$ is selected from an amino acid residue of Leu; $X_{28}$ is selected from an amino acid residue of Ala; $X_{29}$ is selected from an amino acid residue of Gly; $X_{30}$ is selected from an amino acid residue of Gly; Y1 is a Lys, Orn, Dap, Dab or Cys residue with a substituent on the side chain, the substituent having a structure of formula {[2-(2-amino-ethoxy)-ethoxy]-acetyl}$_a$-(y-Glu)$_b$-CO—(CH$_2$)$_c$—COOH; a is an integer of 1-3; b is 1 or 2; c is an integer of 10-30.

Some embodiments of the present disclosure also provide a GLP-1 analog having general formula (I) or a pharmaceutically acceptable salt thereof, wherein $X_1$ is selected from an amino acid residue of Tyr; $X_2$ is selected from the group consisting of amino acid residues of Aib and D-Ala; $X_{10}$ is selected from Y1; $X_{12}$ is selected from an amino acid residue of Ile; $X_{13}$ is selected from an amino acid residue of Tyr; $X_{14}$ is selected from the group consisting of amino acid residues of Leu and Nle; $X_{15}$ is selected from an amino acid residue of Glu; $X_{16}$ is selected from the group consisting of amino acid residues of Arg and Lys; $X_{17}$ is selected from an amino acid residue of Ile; $X_{18}$ is selected from an amino acid residue of Ala; $X_{19}$ is selected from an amino acid residue of Ala; $X_{20}$ is selected from the group consisting of amino acid residues of Gln and Lys; $X_{23}$ is selected from the group consisting of amino acid residues of Ile and Val; $X_{24}$ is selected from the group consisting of amino acid residues of Asn and Gln; $X_{27}$ is selected from the group consisting of amino acid residues of Ile and Leu; $X_{28}$ is selected from an amino acid residue of Ala; $X_{29}$ is selected from an amino acid residue of Gly; $X_{30}$ is selected from an amino acid residue of Gly; Y1 is a Lys, Orn, Dap, Dab or Cys residue with a substituent on the side chain, the substituent having a structure of formula {[2-(2-amino-ethoxy)-ethoxy]-acetyl}$_a$-(y-Glu)$_b$ (CH$_2$)$_c$—COOH; wherein: a is an integer of 1-3; b is 1 or 2; c is an integer of 10-30.

Some embodiments of the present disclosure also provide a GLP-1 analog having general formula (I) or a pharmaceutically acceptable salt thereof, wherein $X_1$ is selected from an amino acid residue of Tyr; $X_2$ is selected from the group consisting of amino acid residues of Aib and D-Ala; $X_{10}$ is selected from an amino acid residue of Tyr; $X_{12}$ is selected from Y1; $X_{13}$ is selected from an amino acid residue of Tyr; $X_{14}$ is selected from the group consisting of amino acid residues of Leu and Nle; $X_{15}$ is selected from an amino acid residue of Glu; $X_{16}$ is selected from the group consisting of amino acid residues of Arg and Lys; $X_{17}$ is selected from an amino acid residue of Ile; $X_{18}$ is selected from an amino acid residue of Ala; $X_{19}$ is selected from an amino acid residue of Ala; $X_{20}$ is selected from the group consisting of amino acid residues of Gln and Lys; $X_{23}$ is selected from the group consisting of amino acid residues of Ile and Val; $X_{24}$ is selected from the group consisting of amino acid residues of Asn and Gln; $X_{27}$ is selected from the group consisting of amino acid residues of Ile and Leu; $X_{28}$ is selected from an amino acid residue of Ala; $X_{29}$ is selected from an amino acid residue of Gly; $X_{30}$ is selected from an amino acid residue of Gly; Y1 is a Lys, Orn, Dap, Dab or Cys residue with a substituent on the side chain, the substituent having a structure of formula {[2-(2-amino-ethoxy)-ethoxy]-acetyl}$_a$-(y-Glu)$_b$-CO—(CH$_2$)$_c$—COOH; wherein: a is an integer of 1-3; b is 1 or 2; c is an integer of 10-30.

Some embodiments of the present disclosure also provide a GLP-1 analog having general formula (I) or a pharmaceutically acceptable salt thereof, wherein $X_1$ is selected from an amino acid residue of Tyr; $X_2$ is selected from the group consisting of amino acid residues of Aib and D-Ala; $X_{10}$ is selected from an amino acid residue of Tyr; $X_{12}$ is selected from an amino acid residue of Ile; $X_{13}$ is selected from Y1; $X_{14}$ is selected from the group consisting of amino acid residues of Leu and Nle; $X_{18}$ is selected from an amino acid residue of Glu; $X_{16}$ is selected from the group consisting of amino acid residues of Arg and Lys; $X_{17}$ is selected from an amino acid residue of Ile; $X_{18}$ is selected from an amino acid residue of Ala; $X_{19}$ is selected from an amino acid residue of Ala; $X_{20}$ is selected from the group consisting of amino acid residues of Gln and Lys; $X_{23}$ is selected from the group consisting of amino acid residues of Ile and Val; $X_{24}$ is selected from the group consisting of amino acid residues of Asn and Gln; $X_{27}$ is selected from the group consisting of amino acid residues of Ile and Leu; $X_{28}$ is selected from an amino acid residue of Ala; $X_{29}$ is selected from an amino acid residue of Gly; $X_{30}$ is selected from an amino acid residue of Gly; Y1 is a Lys, Orn, Dap, Dab or Cys residue with a substituent on the side chain, the substituent having a structure of formula {[2-(2-amino-ethoxy)-ethoxy]-acetyl}$_a$-(y-Glu)$_b$-CO—(CH$_2$)$_c$—COOH; wherein: a is an integer of 1-3; b is 1 or 2; c is an integer of 10-30.

Some embodiments of the present disclosure also provide a GLP-1 analog having general formula (I) or a pharmaceutically acceptable salt thereof, wherein $X_1$ is selected from an amino acid residue of Tyr; $X_2$ is selected from the group consisting of amino acid residues of Aib and D-Ala; $X_{10}$ is selected from an amino acid residue of Tyr; $X_{12}$ is selected from an amino acid residue of Ile; $X_{13}$ is selected from an amino acid residue of Tyr; $X_{14}$ is selected from Y1; $X_{15}$ is selected from an amino acid residue of Glu; $X_{16}$ is selected from the group consisting of amino acid residues of Arg and Lys; $X_{17}$ is selected from an amino acid residue of Ile; $X_{18}$ is selected from an amino acid residue of Ala; $X_{19}$ is selected from an amino acid residue of Ala; $X_{20}$ is selected from the group consisting of amino acid residues of Gln and Lys; $X_{23}$ is selected from the group consisting of amino acid residues of Ile and Val; $X_{24}$ is selected from the group consisting of amino acid residues of Asn and Gln; $X_{27}$ is selected from the group consisting of amino acid residues of Ile and Leu; $X_{28}$ is selected from an amino acid residue of Ala; $X_{29}$ is selected from an amino acid residue of Gly; $X_{30}$ is selected from an amino acid residue of Gly; Y1 is a Lys, Orn, Dap, Dab or Cys residue with a substituent on the side chain, the substituent having a structure of formula {[2-(2-amino-ethoxy)-ethoxy]-acetyl}$_a$-(y-Glu)$_b$-CO—(CH$_2$)$_c$—COOH; wherein: a is an integer of 1-3; b is 1 or 2; c is an integer of 10-30.

Some embodiments of the present disclosure also provide a GLP-1 analog having general formula (I) or a pharmaceutically acceptable salt thereof, wherein $X_1$ is selected from an amino acid residue of Tyr; $X_2$ is selected from an amino acid residue of Aib; $X_{10}$ is selected from an amino acid residue of Tyr; $X_{12}$ is selected from an amino acid residue of Ile; $X_{13}$ is selected from an amino acid residue of Tyr; $X_{14}$ is selected from Y1; $X_{15}$ is selected from an amino acid residue of Glu; $X_{16}$ is selected from the group consisting of amino acid residues of Arg and Lys; $X_{17}$ is selected from an amino acid residue of Ile; $X_{18}$ is selected from an amino acid residue of Ala; $X_{19}$ is selected from an amino acid residue of Ala; $X_{20}$ is selected from an amino acid residue of Gln; $X_{23}$ is selected from the group consisting of amino acid residues of Ile and Val; $X_{24}$ is selected from an amino acid residue of Asn; $X_{27}$ is selected from the group consisting of amino acid residues of Ile and Leu; $X_{28}$ is selected from an amino acid residue of Ala; $X_{29}$ is selected from an amino acid residue of Gly; $X_{30}$ is selected from an amino acid residue of Gly; Y1 is a Lys, Orn, Dap, Dab or Cys residue with a substituent on the side chain, the substituent having a structure of formula {[2-(2-amino-ethoxy)-ethoxy]-acetyl}$_a$-(y-Glu)$_b$-CO—(CH$_2$)$_c$—COOH; a is an integer of 1-3; b is 1 or 2; c is an integer of 10-30.

Some embodiments of the present disclosure also provide a GLP-1 analog having general formula (I) or a pharmaceutically acceptable salt thereof, wherein $X_1$ is selected from an amino acid residue of Tyr; $X_2$ is selected from the group consisting of amino acid residues of Aib and D-Ala; $X_{10}$ is selected from an amino acid residue of Tyr; $X_{12}$ is selected from an amino acid residue of Ile; $X_{13}$ is selected from an amino acid residue of Tyr; $X_{14}$ is selected from the group consisting of amino acid residues of Leu and Nle; $X_{15}$ is selected from an amino acid residue of Glu; $X_{16}$ is selected from Y1; $X_{17}$ is selected from an amino acid residue of Ile; $X_{18}$ is selected from an amino acid residue of Ala; $X_{19}$ is selected from an amino acid residue of Ala; $X_{20}$ is selected from the group consisting of amino acid residues of Gln and Lys; $X_{23}$ is selected from the group consisting of amino acid residues of Ile and Val; $X_{24}$ is selected from the group consisting of amino acid residues of Asn and Gln; $X_{27}$ is selected from the group consisting of amino acid residues of Ile and Leu; $X_{28}$ is selected from an amino acid residue of Ala; $X_{29}$ is selected from an amino acid residue of Gly; $X_{30}$ is selected from an amino acid residue of Gly; Y1 is a Lys, Orn, Dap, Dab or Cys residue with a substituent on the side chain, the substituent having a structure of formula {[2-(2-amino-ethoxy)-ethoxy]-acetyl}$_a$-(y-Glu)$_b$-CO—(CH$_2$)$_c$—COOH; wherein: a is an integer of 1-3; b is 1 or 2; c is an integer of 10-30.

Some embodiments of the present disclosure also provide a GLP-1 analog having general formula (I) or a pharmaceutically acceptable salt thereof, wherein $X_1$ is selected from an amino acid residue of Tyr; $X_2$ is selected from the group consisting of amino acid residues of Aib and D-Ala; $X_{10}$ is selected from an amino acid residue of Tyr; $X_{12}$ is selected from an amino acid residue of Ile; $X_{13}$ is selected from an amino acid residue of Tyr; $X_{14}$ is selected from the group consisting of amino acids of Leu and Nle; $X_{18}$ is selected from an amino acid residue of Glu; $X_{16}$ is selected from the group consisting of amino acid residues of Arg and Lys; $X_{17}$ is selected from Y1; $X_{18}$ is selected from an amino acid residue of Ala; $X_{19}$ is selected from an amino acid residue of Ala; $X_{20}$ is selected from the group consisting of amino acid residues of Gln and Lys; $X_{23}$ is selected from the group consisting of amino acid residues of Ile and Val; $X_{24}$ is selected from the group consisting of amino acid residues of Asn and Gln; $X_{27}$ is selected from the group consisting of amino acid residues of Ile and Leu; $X_{28}$ is selected from an amino acid residue of Ala; $X_{29}$ is selected from an amino acid residue of Gly; $X_{30}$ is selected from an amino acid residue of Gly; Y1 is a Lys, Om, Dap, Dab or Cys residue with a substituent on the side chain, the substituent having a structure of formula {[2-(2-amino-ethoxy)-ethoxy]-acetyl}$_a$-(y-Glu)$_b$-CO—(CH$_2$)$_c$—COOH; wherein: a is an integer of 1-3; b is 1 or 2; c is an integer of 10-30.

Some embodiments of the present disclosure also provide a GLP-1 analog having general formula (I) or a pharmaceutically acceptable salt thereof, wherein $X_{10}$, $X_{12}$, $X_{13}$, $X_{14}$, $X_{16}$ and $X_{17}$ are each independently selected from Y1; wherein Y1 is a Lys, Om, Dap, Dab or Cys residue with a substituent on the side chain, the substituent having a structure of formula {[2-(2-amino-ethoxy)-ethoxy]-acetyl}$_a$-(y-Glu)$_b$-CO—(CH$_2$)$_c$—COOH; a is an integer of 1-3; b is 1 or 2; c is an integer of 10-30.

Some embodiments of the present disclosure also provide a GLP-1 analog having general formula (I) or a pharmaceutically acceptable salt thereof, wherein a is 2, b is 1 or 2, and c is an integer of 16-20 (reference may be made to 16, 17, 18, 19 or 20).

Some embodiments of the present disclosure also provide a GLP-1 analog having general formula (I) or a pharmaceutically acceptable salt thereof, wherein a is 2, b is 1 or 2, and c is 16, 18 or 20.

Some embodiments of the disclosure also provide a GLP-1 analog having general formula (I) or a pharmaceutically acceptable salt thereof, wherein $X_{10}$ is Y1; Y1 is Lys with a substituent on the side chain, the substituent having a structure of formula {[2-(2-amino-ethoxy)-ethoxy]-acetyl}$_a$-(y-Glu)$_b$-CO—(CH$_2$)$_c$—COOH; a is 2; b is 1 or 2; c is 16 or 18.

Some embodiments of the present disclosure also provide a GLP-1 analog having general formula (I) or a pharmaceutically acceptable salt thereof, wherein $X_{12}$ is Y1; Y1 is Lys with a substituent on the side chain, the substituent having a structure of formula {[2-(2-amino-ethoxy)-ethoxy]-acetyl}$_a$-(y-Glu)$_b$-CO—(CH$_2$)$_c$—COOH; a is 2; b is 1 or 2; c is 16 or 18.

Some embodiments of the present disclosure also provide a GLP-1 analog having general formula (I) or a pharmaceutically acceptable salt thereof, wherein $X_{13}$ is Y1; Y1 is Lys with a substituent on the side chain, the substituent having a structure of formula {[2-(2-amino-ethoxy)-ethoxy]-acetyl}$_a$-(y-Glu)$_b$-CO—(CH$_2$)$_c$—COOH; a is 2; b is 1 or 2; c is 16 or 18.

Some embodiments of the disclosure also provide a GLP-1 analog having general formula (I) or a pharmaceutically acceptable salt thereof, wherein $X_{14}$ is Y1; Y1 is Lys with a substituent on the side chain, the substituent having a structure of formula {[2-(2-amino-ethoxy)-ethoxy]-acetyl}$_a$-(y-Glu)$_b$-CO—(CH$_2$)$_c$—COOH; a is 2; b is 1 or 2; c is 16 or 18.

Some embodiments of the present disclosure also provide a GLP-1 analog having general formula (I) or a pharmaceutically acceptable salt thereof, wherein $X_{16}$ is Y1; Y1 is Lys with a substituent on the side chain, the substituent having a structure of formula {[2-(2-amino-ethoxy)-ethoxy]-acetyl}$_a$-(y-Glu)$_b$-CO—(CH$_2$)$_c$—COOH; a is 2; b is 1 or 2; c is 16 or 18.

Some embodiments of the present disclosure also provide a GLP-1 analog having general formula (I) or a pharmaceutically acceptable salt thereof, wherein $X_{17}$ is Y1; Y1 is Lys with a substituent on the side chain, the substituent having a structure of formula {[2-(2-amino-ethoxy)-ethoxy]-acetyl}$_a$-(y-Glu)$_b$-CO—(CH$_2$)$_c$—COOH; a is 2; b is 1 or 2; c is 16 or 18.

Some embodiments of the present disclosure also provide a GLP-1 analog having general formula (I) or a pharmaceutically acceptable salt thereof, wherein the side chain amino group of the Lys residue in Y1 is covalently connected to a substituent by formation of an amide bond.

Some embodiments of the present disclosure also provide a GLP-1 analog having general formula (I) or a pharmaceutically acceptable salt thereof, wherein Y1 is K(-OEG-OEG-yGlu-C18-OH) or K(-OEG-OEG-yGlu-C20-OH), wherein K(-OEG-OEG-yGlu-C18-OH) has a structure shown below:

and K(-OEG-OEG-yGlu-C20-OH) has a structure shown below:

-continued

Some embodiments of the present disclosure also provide a GLP-1 analog having general formula (I) or a pharmaceutically acceptable salt thereof, wherein Y1 is K(-OEG-OEG-yGlu-C18-OH) or K(-OEG-OEG-yGlu-C20-OH), wherein: K(-OEG-OEG-vGlu-C18-OH) has a structure shown below:

tically acceptable salt thereof, wherein $X_1$ is selected from an amino acid residue of Tyr; $X_2$ is selected from an amino acid residue of Aib; $X_{10}$ is selected from an amino acid residue of Tyr; $X_{12}$ is selected from an amino acid residue of Ile; $X_{13}$ is selected from an amino acid residue of Tyr; $X_{14}$ K(-OEG-OEG-yGlu-C20-OH) has a structure shown below:

is selected from Y1; $X_{15}$ is selected from the group consisting of amino acid residues of Asp and Glu; $X_{16}$ is selected Some embodiments of the present disclosure also provide a GLP-1 analog having general formula (I) or a pharmaceutically acceptable salt thereof, wherein in Y1, the ε amino of the Lys residue is covalently connected to a substituent by an amide bond, and the α amino of the Lys residue is connected to a peptide chain.

Some embodiments of the present disclosure provide a GLP-1 analog having general formula (I) or a pharmaceufrom the group consisting of amino acid residues of Arg and Lys; $X_{17}$ is selected from an amino acid residue of Ile; $X_{18}$ is selected from an amino acid residue of Ala; $X_{19}$ is selected from an amino acid residue of Ala; $X_{20}$ is selected from an amino acid residue of Gln; $X_{23}$ is selected from the group consisting of amino acid residues of Ile and Val; $X_{24}$ is selected from an amino acid residue of Asn; $X_{27}$ is selected from the group consisting of amino acid residues of Ile and Leu; $X_{28}$ is selected from an amino acid residue of Ala; $X_{29}$ is selected from an amino acid residue of Gly; $X_{30}$ is selected from an amino acid residue of Gly; Y1 is K(-OEG-OEG-yGlu-C18-OH) or K(-OEG-OEG-yGlu-C20-OH), wherein K(-OEG-OEG-yGlu-C18-OH) has a structure shown below:

is selected from Y1; $X_{15}$ is selected from the group consisting of amino acid residues of Asp and Glu; $X_{16}$ is selected from the group consisting of amino acid residues of Arg and Lys; $X_{17}$ is selected from an amino acid residue of Ile; $X_{18}$ is selected from an amino acid residue of Ala; $X_{19}$ is selected and K(-OEG-OEG-yGlu-C20-OH) has a structure shown below:

from an amino acid residue of Ala; $X_{20}$ is selected from an amino acid residue of Gln; $X_{23}$ is selected from the group Some embodiments of the present disclosure provide a GLP-1 analog having general formula (I) or a pharmaceutically acceptable salt thereof, wherein $X_1$ is selected from an amino acid residue of Tyr; $X_2$ is selected from an amino acid residue of Aib; $X_{10}$ is selected from an amino acid residue of Tyr; $X_{12}$ is selected from an amino acid residue of Ile; $X_{13}$ is selected from an amino acid residue of Tyr; $X_{14}$ consisting of amino acid residues of Ile and Val; $X_{24}$ is selected from an amino acid residue of Asn; $X_{27}$ is selected from the group consisting of amino acid residues of Ile and Leu; $X_{28}$ is selected from an amino acid residue of Ala; $X_{29}$ is selected from an amino acid residue of Gly; $X_{30}$ is selected from an amino acid residue of Gly; Y1 is K(-OEG-OEG-yGlu-C18-OH) or K(-OEG-OEG-yGlu-C20-OH), wherein K(-OEG-OEG-yGlu-C18-OH) has a structure shown below:

K(-OEG-OEG-yGlu-C20-OH) has a structure shown below:

Some embodiments of the present disclosure also provide a GLP-1 analog having general formula (I) or a pharmaceutically acceptable salt thereof, wherein the GLP-1 analog is shown in a general formula (II) (SEQ ID NO: 20): H-YAibEGTFTSDYSIYX$_{14}$X$_{15}$X$_{16}$IAAQEFX$_{23}$NW LX$_{27}$AGGPSSGAPPPS-NH$_2$ (II), wherein X$_{14}$ is K or L, X$_{15}$ is D or E, X$_{16}$ is K or R, X$_{23}$ is V or I, and X$_{27}$ is I or L.

Some embodiments of the present disclosure also provide a GLP-1 analog having general formula (I) or a pharmaceutically acceptable salt thereof, wherein the GLP-1 analog is selected from the group consisting of the compounds shown as numbers 1-18 below:

| SEQ ID NO | Sequence |
|---|---|
| 1 | H-YAibEGTFTSDYSIYKDKIAA QEFVNWLIAGGPSSGAPPPS-NH$_2$ |
| 2 | H-YAibEGTFTSDYSIYKDRIAA QEFVNWLIAGGPSSGAPPPS-NH$_2$ |

-continued

| SEQ ID NO | Sequence |
|---|---|
| 3 | H-YAibEGTFTSDYSIYKDKIAA QEFINWLIAGGPSSGAPPPS-NH$_2$ |
| 4 | H-YAibEGTFTSDYSIYKDRIAA QEFINWLIAGGPSSGAPPPS-NH$_2$ |
| 5 | H-YAibEGTFTSDYSIYKDKIAA QEFINWLLAGGPSSGAPPPS-NH$_2$ |
| 6 | H-YAibEGTFTSDYSIYKDRIAA QEFVNWLLAGGPSSGAPPPS-NH$_2$ |
| 7 | H-YAibEGTFTSDYSIYKDKIAA QEFVNWLLAGGPSSGAPPPS-NH$_2$ |
| 8 | H-YAibEGTFTSDYSIYLEKIAA QEFVNWLLAGGPSSGAPPPS-NH$_2$ |
| 9 | H-YAibEGTFTSDYSIYLEKIAA QEFVNWLIAGGPSSGAPPPS-NH$_2$ |

-continued

| SEQ ID NO | Sequence |
|---|---|
| 10 | H-YAibEGTFTSDYSIYLEKIAA QEFINWLIAGGPSSGAPPPS-NH$_2$ |
| 11 | H-YAibEGTFTSDYSIYLEKIAA QEFINWLLAGGPSSGAPPPS-NH$_2$ |
| 12 | H-YAibEGTFTSDYSIYKEKIAA QEFVNWLIAGGPSSGAPPPS-NH$_2$ |
| 13 | H-YAibEGTFTSDYSIYKERIAA QEFVNWLIAGGPSSGAPPPS-NH$_2$ |
| 14 | H-YAibEGTFTSDYSIYKEKIAA QEFINWLIAGGPSSGAPPPS-NH$_2$ |
| 15 | H-YAibEGTFTSDYSIYKERIAA QEFINWLIAGGPSSGAPPPS-NH$_2$ |
| 16 | H-YAibEGTFTSDYSIYKEKIAA QEFINWLLAGGPSSGAPPPS-NH$_2$ |
| 17 | H-YAibEGTFTSDYSIYKERIAA QEFVNWLLAGGPSSGAPPPS-NH$_2$ |
| 18 | H-YAibEGTFTSDYSIYKEKIAA QEFVNWLLAGGPSSGAPPPS-NH$_2$. |

Some embodiments of the present disclosure also provide a GLP-1 analog having general formula (I) or a pharmaceutically acceptable salt thereof, wherein GLP-1 analog is selected from the group consisting of compounds shown as numbers 1 #-18 # below:

| No. | Sequence |
|---|---|
| 1# | H-YAibEGTFTSDYSIYK(OEG-OEG-yGlu-C20-OH)DKIAAQEFVNWLIAGGPSSGAPPPS-NH$_2$ |
| 2# | H-YAibEGTFTSDYSIYK(OEG-OEG-yGlu-C20-OH)DRIAAQEFVNWLIAGGPSSGAPPPS-NH$_2$ |
| 3# | H-YAibEGTFTSDYSIYK(OEG-OEG-yGlu-C20-OH)DKIAAQEFINWLIAGGPSSGAPPPS-NH$_2$ |
| 4# | H-YAibEGTFTSDYSIYK(OEG-OEG-yGlu-C20-OH)DRIAAQEFINWLIAGGPSSGAPPPS-NH$_2$ |
| 5# | H-YAibEGTFTSDYSIYK(OEG-OEG-yGlu-C20-OH)DKIAAQEFINWLLAGGPSSGAPPPS-NH$_2$ |
| 6# | H-YAibEGTFTSDYSIYK(OEG-OEG-yGlu-C20-OH)DRIAAQEFVNWLLAGGPSSGAPPPS-NH$_2$ |
| 7# | H-YAibEGTFTSDYSIYK(OEG-OEG-yGlu-C20-OH)DKIAAQEFVNWLLAGGPSSGAPPPS-NH$_2$ |
| 8# | H-YAibEGTFTSDYSIYLEK(OEG-OEG-yGlu-C20-OH)IAAQEFVNWLLAGGPSSGAPPPS-NH$_2$ |
| 9# | H-YAibEGTFTSDYSIYLEK(OEG-OEG-yGlu-C20-OH)IAAQEFVNWLIAGGPSSGAPPPS-NH$_2$ |
| 10# | H-YAibEGTFTSDYSIYLEK(OEG-OEG-yGlu-C20-OH)IAAQEFINWLIAGGPSSGAPPPS-NH$_2$ |
| 11# | H-YAibEGTFTSDYSIYLEK(OEG-OEG-yGlu-C20-OH)IAAQEFINWLLAGGPSSGAPPPS-NH$_2$ |
| 12# | H-YAibEGTFTSDYSIYK(OEG-OEG-yGlu-C20-OH)EKIAAQEFVNWLIAGGPSSGAPPPS-NH$_2$ |
| 13# | H-YAibEGTFTSDYSIYK(OEG-OEG-yGlu-C20-OH)ERIAAQEFVNWLIAGGPSSGAPPPS-NH$_2$ |

-continued

| No. | Sequence |
|---|---|
| 14# | H-YAibEGTFTSDYSIYK(OEG-OEG-yGlu-C20-OH)EKIAAQEFINWLIAGGPSSGAPPPS-NH$_2$ |
| 15# | H-YAibEGTFTSDYSIYK(OEG-OEG-yGlu-C20-OH)ERIAAQEFINWLIAGGPSSGAPPPS-NH$_2$ |
| 16# | H-YAibEGTFTSDYSIYK(OEG-OEG-yGlu-C20-OH)EKIAAQEFINWLLAGGPSSGAPPPS-NH$_2$ |
| 17# | H-YAibEGTFTSDYSIYK(OEG-OEG-yGlu-C20-OH)ERIAAQEFVNWLLAGGPSSGAPPPS-NH$_2$ |
| 18# | H-YAibEGTFTSDYSIYK(OEG-OEG-yGlu-C20-OH)EKIAAQEFVNWLLAGGPSSGAPPPS-NH$_2$. |

In some embodiments, the GLP-1 analog of the present disclosure is selected from the group consisting of compounds shown as 7 #, 12 #, 13 #, 14 #, 15 #, 16 #, 17 #, and 18 # in FIG. 3.

Some embodiments of the present disclosure also provide a pharmaceutical composition comprising:

1) a GLP-1 analog having general formula (I) or a pharmaceutically acceptable salt thereof, and
2) a pharmaceutically acceptable excipient or a pharmaceutical carrier.

In some specific embodiments, the pharmaceutical composition may contain 0.01 wt % to 99 wt % of the GLP-1 analog in a unit dose, or the pharmaceutical composition may contain 0.1-2000 mg, and in some specific embodiments, 1-1000 mg of the GLP-1 analog in a unit dose.

Some embodiments of the present disclosure also provide use of the GLP-1 analog having general formula (I) or the pharmaceutically acceptable salt thereof, and the pharmaceutical composition comprising the same, in preparing a medicament for the treatment of non-insulin-dependent diabetes/type II diabetes, insulin-dependent diabetes, obesity, non-alcoholic fatty liver, hepatic steatosis, dyslipidemia associated with insulin resistance, and/or dyslipidemia associated with diabetes.

Some embodiments of the present disclosure provide use of the GLP-1 analog having general formula (I) or a pharmaceutically acceptable salt thereof as a medicament.

Some embodiments of the present disclosure provide use of the GLP-1 analog having general formula (I) or a pharmaceutically acceptable salt thereof as a medicament for the treatment of non-insulin-dependent diabetes/type II diabetes, insulin-dependent diabetes, obesity, non-alcoholic fatty liver, hepatic steatosis, dyslipidemia associated with insulin resistance, and/or dyslipidemia associated with diabetes.

Some embodiments of the present disclosure provide a method for treating non-insulin-dependent diabetes/type II diabetes, insulin-dependent diabetes, obesity, non-alcoholic fatty liver, hepatic steatosis, dyslipidemia associated with insulin resistance, and/or dyslipidemia associated with diabetes, which comprises administering to a subject in need thereof the GLP-1 analog having general formula (I) and the pharmaceutically acceptable salt thereof, or the pharmaceutical composition comprising the same.

The present disclosure provides a compound capable of simultaneously activating a GLP-1 receptor and a GIP receptor, and in some embodiments, the GLP-1 analog have greater agonist activity for the GLP-1R than for the GIP receptor.

In some specific embodiments, the GLP-1 analog of the present disclosure has a ratio of the agonist activity against the GLP-1R to the agonist activity against the GIP receptor of (1-10):1, (1.1-10):1, (1.1-9.5):1, (1.1-9):1, (1.1-8.5):1, (1.1-8):1, (1.1-7.5):1, (1.1-7):1, (1.1-6.5):1, (1.1-6):1, (1.2-10):1, (1.2-9.5):1, (1.2-9):1, (1.2-8.5):1, (1.2-8):1, (1.2-7.5):1, (1.2-7):1, (1.2-6.5):1, (1.2-6):1, (1.3-10):1, (1.3-9.5):1, (1.3-9):1, (1.3-8.5):1, (1.3-8):1, (1.3-7.5):1, (1.3-7):1, (1.3-6.5):1, (1.3-6):1, (1.4-10):1, (1.4-9.5):1, (1.4-9):1, (1.4-8.5): 1, (1.4-8):1, (1.4-7.5):1, (1.4-7): 1, (1.4-6.5):1, (1.4-6):1, (1.5-10):1, (1.5-9.5):1, (1.5-9):1, (1.5-8.5):1, (1.5-8):1, (1.5-7.5):1, (1.5-7):1, (1.5-6.5):1, (1.5-6):1, (2-10):1, (2-9.5):1, (2-9):1, (2-8.5):1, (2-8):1, (2-7.5):1, (2-7):1, (2-6.5):1, (2-6): 1, (2.5-10):1, (2.5-9.5):1, (2.5-9):1, (2.5-8.5):1, (2.5-8):1, (2.5-7.5):1, (2.5-7):1, (2.5-6.5):1, (2.5-6):1, (3-10):1, (3-9.5):1, (3-9):1, (3-8.5):1, (3-8):1, (3-7.5):1, (3-7):1, (3-6.5):1, (3-6):1, (3.5-10):1, (3.5-9.5):1, (3.5-9):1, (3.5-8.5):1, (3.5-8):1, (3.5-7.5):1, (3.5-7):1, (3.5-6.5):1, (3.5-6):1, (4-10):1, (4-9.5):1, (4-9):1, (4-8.5):1, (4- 8):1, (4-7.5):1, (4-7):1, (4-6.5):1, (4-6):1, (4.5-10):1, (4.5-9.5): 1, (4.5-9):1, (4.5-8.5):1, (4.5-8):1, (4.5-7.5):1, (4.5-7):1, (4.5-6.5):1, (4.5-6):1, (5-10):1, (5-9.5):1, (5-9):1, (5- 8.5):1, (5-8):1, (5-7.5):1, (5-7):1, (5-6.5):1, (5-6):1, (5-5.5):1, (5.1-5.5):1, (5.2-5.4):1, (5.2-5.3):1 or any range or point of value therebetween, e.g., about 1:1, about 1.1:1, about 1.2:1, about 1.3:1, about 1.4:1, about 1.5:1, about 2:1, about 2.5:1, about 3:1, about 3.5:1, about 4:1, about 4.5:1, about 5:1, about 5.2:1, about 5.3:1, about 5.4:1, about 5.5:1, about 6:1, about 6.5:1, about 7:1, about 7.5:1, about 8:1, about 8.5:1, about 9:1, about 9.5:1, or about 10:1. The above ratio is a normalized ratio of data from in vitro assay of corresponding agonist activity. For example, the corresponding agonist activity can be determined by a cAMP-Gs kinetic kit. In this context, the expression (1-10):1 and the expression 1:1 to 10:1 have the same meaning.

In another embodiment, the present disclosure provides the above GLP-1 analog and the pharmaceutically acceptable salt thereof. The GLP-1 analog provided by the present disclosure is an amphoteric compound that can exhibit both acidity and basicity. The GLP-1 analog provided by the present disclosure can be reacted with acidic or basic compounds to form salts by those skilled in the art using well known techniques.

The pharmaceutical composition containing the GLP-1 analog according to the present disclosure can be used for treating patients in need of such treatment by parenteral administration. For the parenteral routes of administration, subcutaneous injection, intramuscular injection or intravenous injection may be selected. The polypeptide dualagonist compound of the present disclosure may also be administered by the transdermal route, optionally via an iontophoretic patch; or by the transmucosal route.

The GLP-1 analog provided by the present disclosure are synthesized by a solid-phase synthesis method. As an example, the synthetic vector is Rink-amide MBHA (Xi'an sunresin Tech Ltd.) resin. During the synthesis, the α-amino group of the amino acid derivative used is protected by the Fmoc (fluorenylmethoxycarbonyl) group. As an example, for the side chain of an amino acid, the following protecting groups are selected according to the difference of functional groups: the mercapto group of the cysteine side chain, the amino groups of the asparagine and glutamine side chains, and the imidazolyl group of the histidine side chain are protected by Trt (trityl); the guanidyl group of the arginine side chain is protected by Pbf (2,2,4,6,7-pentamethyldihydrobenzofuran-5-sulfonyl); the indolyl group of the tryptophan side chain and the amino group of the lysine side chain are protected by Boc (tert-butyloxycarbonyl); and the carboxyl group of the aspartic acid and glutamic acid side chains, the hydroxyl group of the threonine side chain, the phenol group of the tyrosine side chain and the hydroxyl group of the serine side chain are protected by t-Bu (tertbutyl). As an example, in the synthesis process, the carboxyl group of the C-terminal amino acid residue of the polypeptide is firstly condensed to the insoluble Rink-amide MBHA polymer resin in the form of an amide bond; then the Fmoc protecting group on the α-amino group is removed using an N,N-dimethylformamide (DMF) solution containing 20% 4-methylpiperidine; and then the solid phase carrier is condensed in excess with the next amino acid derivative in the polypeptide sequence to form an amide bond to extend the peptide chain. The procedures of "condensation-→washing→deprotection→washing→the next round of amino acid condensation" repeated to enable the desired length of the polypeptide chain to be synthesized; finally, a mixed solution of trifluoroacetic acid:water:triisopropylsilane (as an example, 90:5:5, v:v:v) is reacted with the resin to cleave the polypeptide from the solid phase carrier, and the mixture is precipitated using 5 times the volume of frozen methyl tert-butyl ether to obtain a solid crude product of the GLP-1 analog. The crude solid product of the polypeptide is dissolved in an acetonitrile/water mixed solution containing 0.1% trifluoroacetic acid, and purified and separated using a C-18 reversed-phase preparative chromatographic column to obtain a pure product of the GLP-1 analog.

According to some embodiments, the present disclosure also provides a kit-of-parts, which comprises:

the GLP-1 analog or the pharmaceutically acceptable salt thereof according to the present disclosure; and an additional therapeutic agent selected from any one of or a combination of: anti-obesity agent, antidiabetic agent, antihypertensive agent, and lipid-lowering agent; wherein the GLP-1 analog or the pharmaceutically acceptable salt thereof and the additional therapeutic agent are each placed in a separate container. In some embodiments, the GLP-1 analog or the pharmaceutically acceptable salt thereof and the additional therapeutic agent are administered to a subject separately or in combination (e.g., simultaneously or sequentially).

In certain embodiments, the pharmaceutical composition of the present disclosure and an administration device (e.g., a syringe, an injection pen, or an automatic syringe) are provided in combination. As an example, the pharmaceutical composition of the present disclosure is pre-filled in an administration device for self-administration by a subject at home. As another example, the pharmaceutical composition of the present disclosure and an administration device are provided separately.

DETAILED DESCRIPTION

Figure 1:
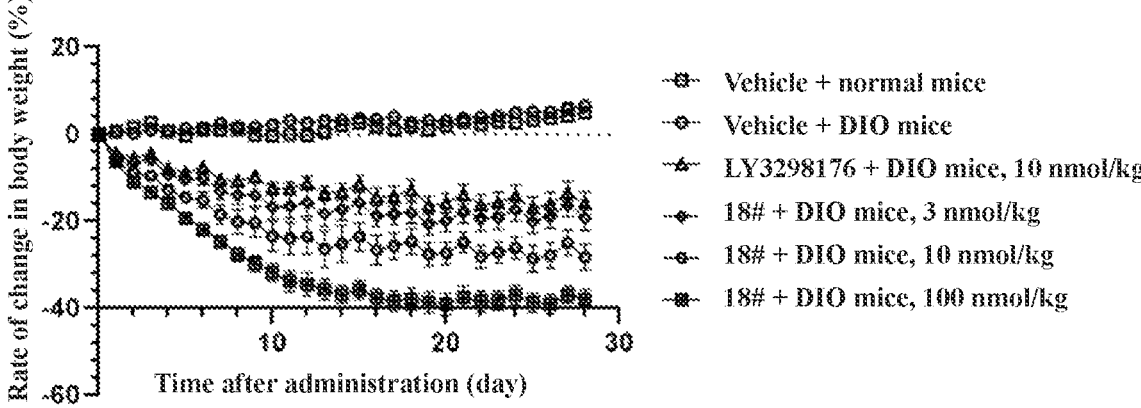
FIG. 1 shows the effect of the compound of the present disclosure on the rate of change in body weight of diet-induced obese mice.

In order to facilitate the understanding of the present disclosure, some technical and scientific terms are specifically defined below. Unless otherwise specifically defined herein, all other technical and scientific terms used herein have the meanings generally understood by those of ordinary skill in the art to which the present disclosure belongs.

The amino acid sequences of the present disclosure contain the standard single-letter or three-letter codes for twenty amino acids, and all amino acid residues in the present disclosure are preferably in the L-configuration unless specifically stated. In addition, Aib refers to α-aminoisobutyric acid, D-Ala refers to D-alanine, Orn refers to ornithine, Dap refers to 2,3-diaminopropionic acid, and Dab refers to 2,4-diaminobutyric acid.

The term "agonist" is defined as a substance having an activating effect on the GLP-1 receptor or on the GIP receptor.

The term "GLP-1/GIP dual-agonist" as used in the context of the present disclosure refers to a substance or ligand that can activate the GLP-1 receptor and the GIP receptor.

In the present disclosure, the term "treat, treating or treatment" includes inhibiting, alleviating, stopping or reversing the progression or severity of an existing symptom or condition.

The term "natural amino acids" refer to 20 conventional amino acids, i.e., alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W), and tyrosine (Y).

The term "unnatural amino acids" refer to amino acids that are not naturally encoded, or are not found in the genetic code of any organism. For example, the unnatural amino acids may be completely synthetic compounds. Examples of the unnatural amino acids include, but are not limited to, hydroxyproline, γ-carboxyglutamic acid, O-serine phosphate, azetidinecarboxylic acid, 2-aminoadipic acid, 3-aminoadipic acid, β-alanine, aminopropionic acid, 2-aminobutyric acid, 4-aminobutyric acid, 6-aminohexanoic acid, 2-aminoheptanoic acid, 2-aminoisobutyric acid, 3-aminoisobutyric acid, 2-aminopimelic acid, t-butylglycine, 2,4-diaminoisobutyric acid (Dap), desmosine, 2,2'-diaminopimelic acid, 2,3-diaminopropionic acid (Dab), N-ethylglycine, N-methylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine (Orn), D-ornithine, D-arginine, p-aminophenylalanine, pentylglycine, pipecolic acid and thioproline. In addition, the term also includes derivatives obtained by chemical modification of the C-terminal carboxyl group (or N-terminal amino group and/or side chain functional group) of a natural amino acid (or unnatural amino acid).

The term "alkyl" refers to a saturated aliphatic hydrocarbon group which is a linear or branched group containing 1 to 20 carbon atoms, e.g., an alkyl group containing 1 to 8 carbon atoms, e.g., an alkyl group containing 1 to 6 carbon atoms, e.g., an alkyl group containing 1 to 3 carbon atoms. Non-limiting examples include methyl, ethyl, n-propyl, iso-propyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various branched isomers thereof, and the like. The alkyl may be, for example, a lower alkyl containing 1 to 6 carbon atoms, and non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl and the like. The alkyl may be substituted or unsubstituted, and when it is substituted, the substitution with a substituent may be performed at any accessible connection site, wherein the substituent may be one or more groups independently selected from the group consisting of the following groups: alkyl, alkenyl, alkynyl, alkoxy, alkylthio, alkylamino, halogen, mercapto, hydroxy, nitro, cyano, cycloalkyl, heterocycloalkyl, aryl, heteroaryl, cycloalkoxy, heterocycloalkoxy, cycloalkylthio, heterocycloalkylthio, oxo, carboxyl and a carboxylate group. The substituted alkyl of the present disclosure may be methyl, ethyl, isopropyl, tert-butyl, haloalkyl, deuterated alkyl, alkoxy-substituted alkyl, or hydroxy-substituted alkyl.

The expressions "X is selected from the group consisting of A, B or C", "X is selected from the group consisting of A, B and C", "X is A, B or C", "X is A, B and C" and the like all carry the same meaning, i.e., X may be any one or more of A, B and C.

The "modification" of the amino acid as described in the present disclosure refers to substitution, addition or deletion of an amino acid, including substitution or addition of any one or more of the 20 natural amino acids.

The term "natural GLP-1" refers to a naturally occurring molecule of the glucagon or exendin family of peptides, wherein: the glucagon family of peptides is encoded by the pre-proglucagon gene and includes three small peptides with high homology, i.e., glucagon (1-29), GLP-1 (1-37), and GLP-2 (1-33); and exendins are peptides expressed in lizards and, like GLP-1, are insulinotropic. In some embodiments, the term "natural GLP-1" also refers to human GLP-1 (7-37) and human GLP-1 (7-36).

The term "GLP-1 analog" refers to a substance having up to 25, up to 24, up to 23, up to 22, up to 21, up to 20, up to 19, up to 18, up to 17, up to 16, up to 15, up to 14, up to 13, up to 12, up to 11, up to 10, up to 9, up to 8, up to 7, up to 6, up to 5, up to 4, up to 3, up to 2, or 1 amino acid modification or chemical modification compared to natural GLP-1 (in particular to human GLP-1 (7-37) and human GLP-1 (7-36)), wherein the amino acid modification may be an amino acid substitution, addition, and/or deletion; and the chemical modification may be a chemical modification with a group selected from the group consisting of the following groups: amide, carbohydrate, alkyl, acyl, ester, a polyethylene glycol (PEG) group, a sialylation group, a glycosylation group, and the like.

The term amino acid "substitution" as described in the present disclosure refers to the substitution of one amino acid residue with a different amino acid residue.

The term "polyethylene glycol" or "PEG" refers to a mixture of polycondensates of ethylene oxide and water, which is present in a linear or branched form and represented by the general formula $H(OCH_2CH_2)_n)OH$, where n is at least equal to 9. Unless further stated, this term includes polymers of polyethylene glycol having an average total molecular weight selected from the group consisting of 5,000 to 40,000 daltons.

The term "fatty acid" refers to a carboxylic acid with an aliphatic long tail (chain), which may be saturated or unsaturated. The fatty acids in the present disclosure are carboxylic acids having a C4-C30 linear or branched aliphatic group.

The term "peptide" as used in the present disclosure encompasses the category of peptides having modified amino and carboxyl termini. For example, an amino acid chain containing a terminal carboxylic acid substituted with an amide group is also included within the amino acid sequence designated as a natural amino acid.

All of the hydrogen atoms described in the present disclosure may be substituted with their isotopes (protium, deuterium, and tritium), and any hydrogen atom in the compound of the present disclosure to which the present disclosure relates may also be substituted with an isotope atom.

The term "optional" or "optionally" means that the event or circumstance subsequently described may, but not necessarily, occur, and that the description includes instances where the event or circumstance occurs or does not occur. For example, the expression "a heterocyclyl group optionally substituted with alkyl" means that the alkyl may be, but not necessarily, present, and includes instances where the heterocyclyl group is or not substituted with the alkyl.

The term "substituted" means that one or more, preferably up to 5, more preferably 1 to 3 hydrogen atoms in the group are independently substituted with a substituent. A substituent is only in its possible chemical position, and those skilled in the art will be able to determine (experimentally or theoretically) possible or impossible substitution without undue efforts. For example, it may be unstable when amino or hydroxy having a free hydrogen is bound to a carbon atom having an unsaturated (e.g., olefinic) bond.

The term "pharmaceutical composition" refers to a mixture containing one or more of the compounds described herein or physiologically/pharmaceutically acceptable salts or prodrugs thereof, and other chemical components, wherein the other components are, for example, physiologically/pharmaceutically acceptable carriers and excipients. The purpose of the pharmaceutical composition is to promote the administration to an organism, which facilitates the absorption of the active ingredient, thereby exerting biological activities.

The term "agonist activity" refers to the ability of the compound according to the present disclosure to activate against the human GIP receptor and the human GLP-1 receptor. In some examples, "agonist activity" is embodied in a relatively active form, and specifically refers to the ratio of the activation ability of the compound of the present disclosure against GLP-1R to that against the GIP receptor.

The term "pharmaceutically acceptable salt" refers to the salts of the compound of the present disclosure, which are safe and effective for use in the body of a mammal and possess the requisite biological activities.

Semaglutide refers to a once-a-week GLP-1 receptor single agonist polypeptide drug developed by Novo Nordisk in Denmark, which is currently approved and marketed in the United States, Japan and the European Union.

LY3298176 refers to a once-a-week GIP receptor/GLP-1 receptor dual-agonist polypeptide drug developed by Eli Lilly, which is currently in phase III clinical trials in several countries. The structure is as follows: YAibEGTFTSDY-SIAibLDKIAQKAFVQWLIAGGPSSGAPPPS-NH$_2$, wherein a fatty acid shown below as is modified on K at position 20.

EXAMPLES

The following specific embodiments are provided herein only for illustrating the present disclosure in more detail, rather than limiting the present disclosure. Experimental procedures without specific conditions indicated in the examples of the present disclosure are generally conducted according to conventional conditions, or according to conditions recommended by the manufacturer of the starting materials or commercial products. Reagents without specific sources indicated are commercially available conventional reagents.

1. Experimental Reagent

TABLE 1

| | Reagents and sources | |
| --- | --- | --- |
| No. | Reagent | Source |
| 1 | Rink-amide MBHA resin | Xi'an sunresin Tech Ltd. |
| 2 | HCTU (O-(6-chloro-1-benzotriazol-1-yl)-N,N,N',N'-tetramethyluronium hexafluorophosphate) | Highfine Tech Ltd., Sunzhou |
| 3 | Fmoc-Aib-OH | GL Biochem |
| 4 | Fmoc-L-Lys(Mtt)-OH | GL Biochem |
| 5 | N,N-dimethylformamide | SinoPharm |
| 6 | Dichloromethane | SinoPharm |
| 7 | Trifluoroacetic acid | SinoPharm |
| 8 | Triisopropylsilane | Sigma-Aldrich |
| 9 | Hexafluoroisopropanol | Sigma-Aldrich |
| 10 | Acetonitrile | Merck-Millipore |
| 11 | Diisopropylethylamine | Sigma-Aldrich |
| 12 | 4-methylpiperidine | TCI Chemicals |
| 13 | Methyl tert-butyl ether | TCI Chemicals |
| 14 | Boc-L-Tyr(tBu)-OH | GL Biochem |
| 15 | Fmoc-NH-PEG$_2$-COOH | GL Biochem |
| 16 | Fmoc-L-Glu-OtBu | GL Biochem |
| 17 | HOOC—(CH$_2$)$_{18}$—COOtBu | ChinaPeptides Co., Ltd, Suzhou |
| 18 | 4-methylmorpholine | TCI Chemicals |

2. Experimental Instruments

TABLE 2

| | Instruments and sources | |
| --- | --- | --- |
| No. | Instrument | Source |
| 1 | H-CLASS analytical ultra performance liquid chromatograph | WATERS |

TABLE 2-continued

| | Instruments and sources | |
|---|---|---|
| No. | Instrument | Source |
| 2 | Agilent 1290-6530 ultra performance liquid chromatograph/mass spectrometer | Agilent |
| 3 | Labconco multifunctional freeze dryer | Thermo-Fisher Scientific |
| 4 | Prep150 preparative high performance liquid chromatograph | WATERS |
| 5 | Prelude-X automatic polypeptide synthesizer | Protein Technology Inc |
| 6 | Multichannel high-speed centrifuge | Sigma |

Example 1. Chemical Synthesis of Compound 18 #

1. Synthesis of Polypeptide Skeleton

Rink-amide MBHA resin (degree of substitution: 0.48 mmole/g, 0.1 mmol) was taken and placed in a polypropylene reaction tube for solid phase synthesis of the polypeptide; N,N-dimethylformamide (DMF, 10 mL) was added to swell the resin for 10 min under nitrogen-blowing; DMF was removed in vacuum, and fresh DMF (10 mL) was added to wash the resin; after repeated washing of the resin twice, the solid phase synthesis of the polypeptide was performed on a Prelude-X automatic polypeptide synthesizer using Fmoc/tBu strategy, in which 10 equivalents of amino acid residues activated by HCTU and 4-methylmorpholine (molar ratio of HCTU to 4-methylmorpholine to amino acid residues was 1:2:1) were reacted in DMF at room temperature for 25 min for amide bond condensation, so as to achieve coupling. Deprotection of the N-terminal Fmoc protecting group was performed by 2 reactions (10 min each) at room temperature using a DMF solution containing 20% 4-methylpiperidine. In the synthesis of a polypeptide skeleton, the N-terminal amino acid residue was constructed using Boc-L-Tyr (tBu)-OH and subjected to secondary condensation, which was necessary for improving the quality of a crude peptide.

2. Selective Deprotection of Resin-Peptide Protecting Group Mtt and Fatty Acid Modification of Side Chain After the extension of the polypeptide skeleton (or called resin-peptide) was completed, a mixed solution (10 mL) of dichloromethane containing 30% hexafluoroisopropanol was added, and the mixture was shaken at room temperature for 45 min, and then the mixed solution was removed; a mixed solution (10 mL) of methylene chloride containing 30% hexafluoroisopropanol was added, and the mixture was shaken at room temperature for 45 min, and then the mixed solution was removed. After the reaction was completed, the resin was washed 6 times with DMF. The lysine side chain at position 14 was extended using a Prelude-X automatic polypeptide synthesizer, with an additional coupling/deprotection cycle involving the amino acid components Fmoc-NH-PEG$_2$-COOH and Fmoc-L-Glu-OtBu. All couplings were performed in DMF at room temperature for 25 min using 10 equivalents of amino acid residues activated by HCTU and 4-methylmorpholine (molar ratio of HCTU to 4-methylmorpholine to amino acid residues was 1:2:1). Deprotection of the N-terminal Fmoc protecting group was performed by 2 reactions (10 min each) at room temperature using a DMF solution containing 20% 4-methylpiperidine. After the finally obtained resin was washed three times with DCM and DMF separately, a mixed solution (8 mL) of DMF containing 10 equivalents of HOOC—(CH$_2$)$_{18}$—COOtBu, 10 equivalents of HCTU and 20 equivalents of diisopropylethylamine (DIEA) was added, and the mixture was reacted at room temperature for 4 h to complete the fatty acid modification of the side chain.

3. Product Cleavage

The resin-peptide obtained in the previous step was washed 3 times with DMF and DCM sequentially and dried in vacuum, followed by the addition of a freshly prepared cleavage buffer (trifluoroacetic acid:triisopropylsilane:water=90:5:5, v:v:v), and the mixture was shaken at room temperature for 3-4 h. After the reaction was completed, the mixture was filtered and the resin was washed twice with trifluoroacetic acid. The filtrates were combined before a large amount of frozen methyl tert-butyl ether was added to precipitate a solid. The mixture was centrifuged and the supernatant was discarded to obtain a crude polypeptide of compound 18 #.

4. Purification by Reverse-Phase Liquid Chromatography

Figure 3:
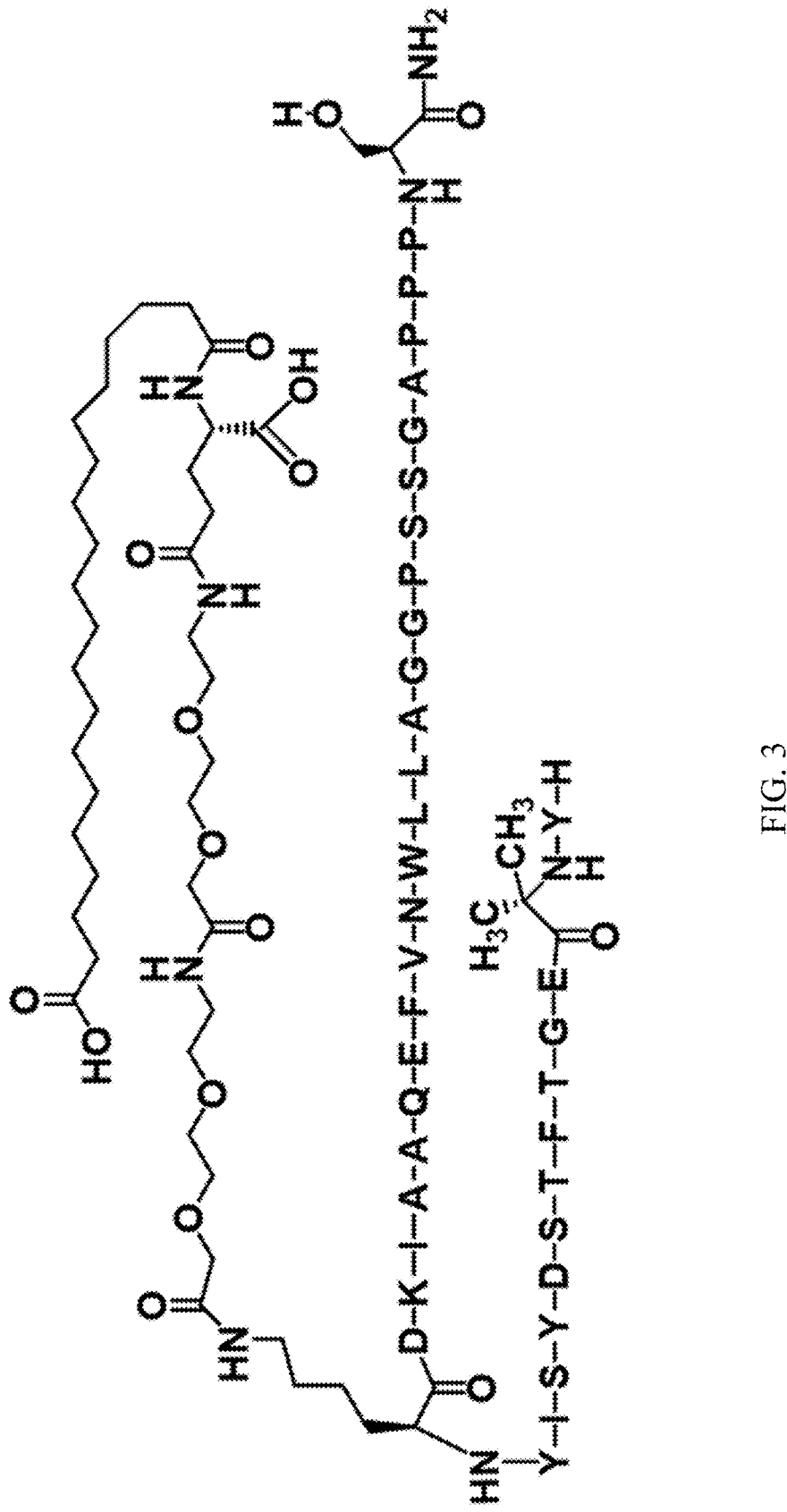
FIG. 3 shows the structures of exemplary compounds of the present disclosure.
Figure 3:
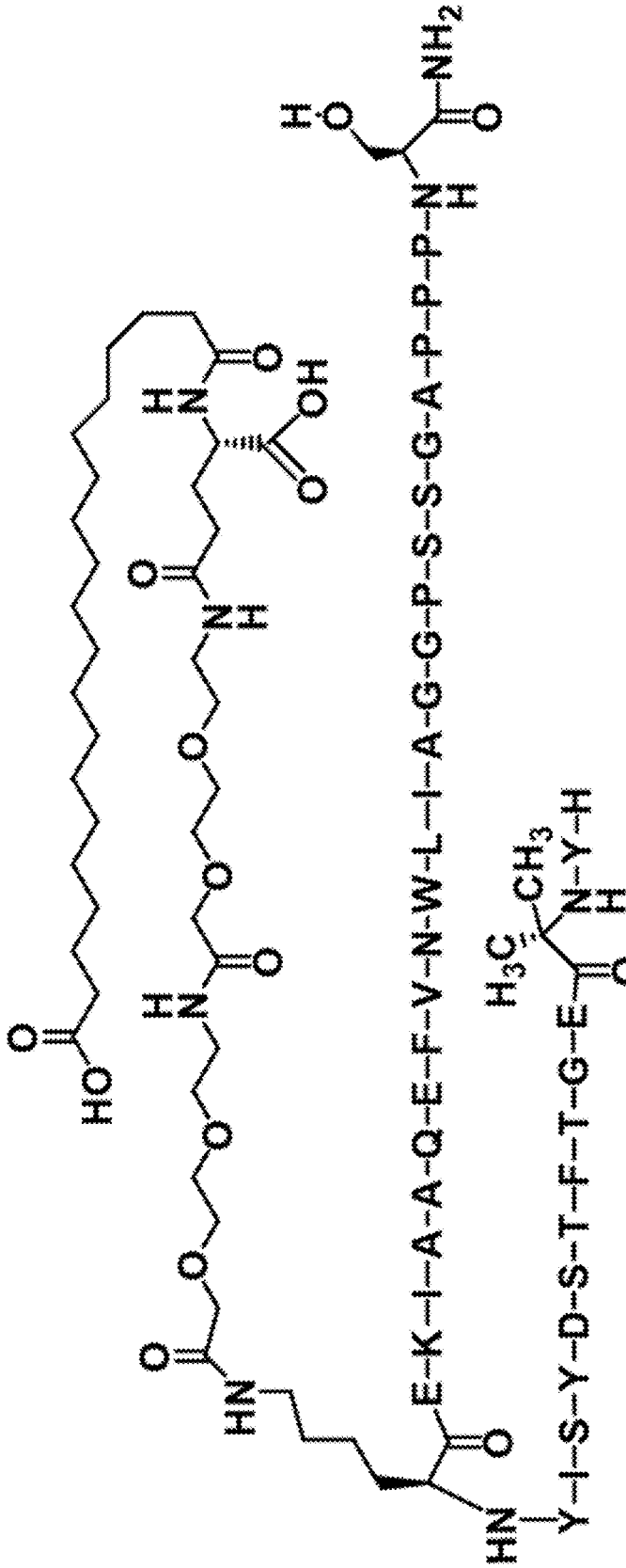
Figure 3:
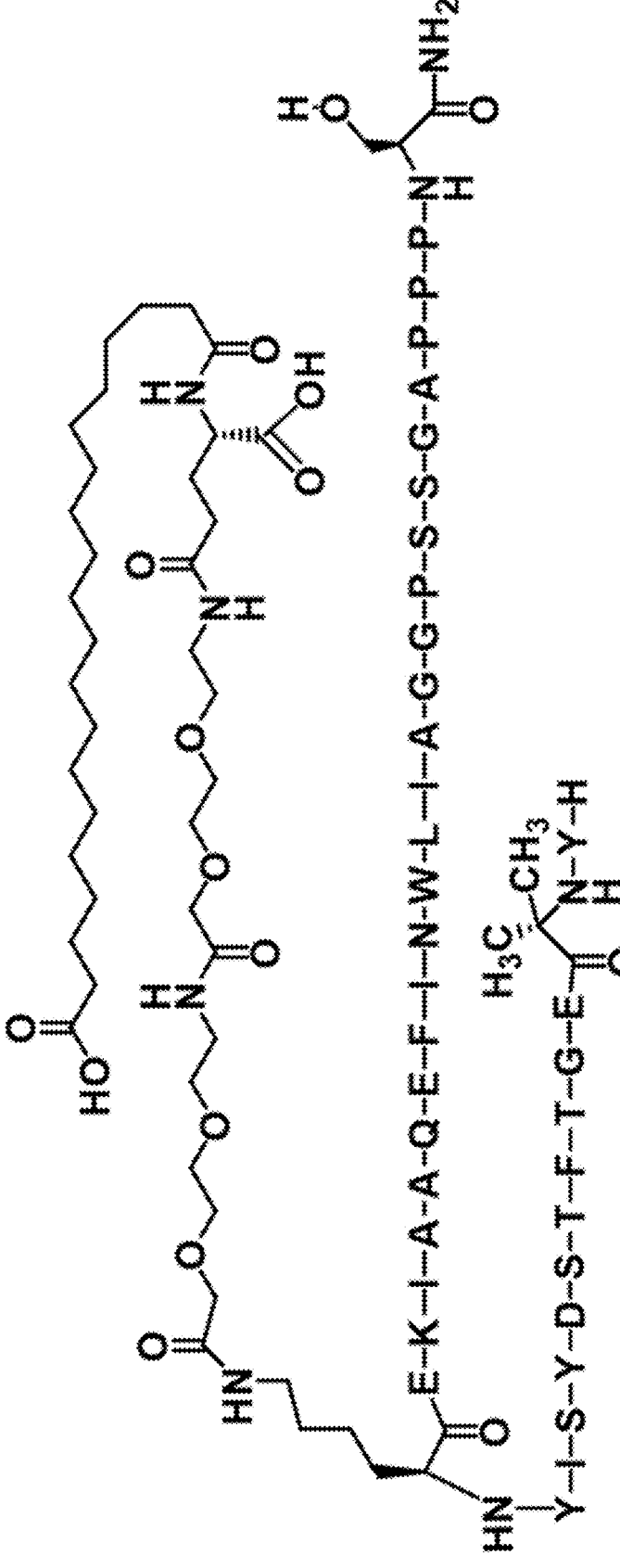

The crude polypeptide of compound 18 # was dissolved in a mixed solvent containing 0.1% trifluoroacetic acid, 20% acetonitrile and 20% acetic acid/water, and the solution was filtered through a 0.22 μm membrane; the filtrate was separated using a WATERS Prep150 LC reverse-phase high performance liquid chromatography system with buffers A (0.1% trifluoroacetic acid, 10% acetonitrile and water) and B (0.1% trifluoroacetic acid, 90% acetonitrile and water). The chromatographic column was an X-SELECT OBD C-18 reverse-phase chromatographic column, and in the purification process, the detection wavelength of the chromatograph was set as 220 nm, and the flow rate was 15 mL/min. The related fractions of the product were collected and freeze-dried to obtain a pure polypeptide product of compound 1 #, with the yield of 18%. The purity of the pure polypeptide product was determined by a combination of analytical high performance liquid chromatography and ultra performance liquid chromatography/mass spectrometry, with the purity of 92.81%. The molecular structure of compound 18 # was H-YAibEGTFTSDYSIYK(OEG-OEG-yGlu-C20-OH)EKIAAQEFVNWLLAGGPSSGAPPPS-NH$_2$, with the structural formula shown as the structure of 18 # in FIG. 3.

Example 2. Chemical Synthesis of Other Compounds

The compounds in Table 3 were synthesized using the experimental protocol of Example 1.

TABLE 3

| | Compounds of the present disclosure |
|---|---|
| Compound No. | Molecular structure |
| 1# | H-YAibEGTFTSDYSIYK(OEG-OEG-yGlu-C20-OH) DKIAAQEFVNWLIAGGPSSGAPPPS-NH$_2$ |
| 2# | H-YAibEGTFTSDYSIYK(OEG-OEG-yGlu-C20-OH) DRIAAQEFVNWLIAGGPSSGAPPPS-NH$_2$ |
| 3# | H-YAibEGTFTSDYSIYK(OEG-OEG-yGlu-C20-OH) DKIAAQEFINWLIAGGPSSGAPPPS-NH$_2$ |
| 4# | H-YAibEGTFTSDYSIYK(OEG-OEG-yGlu-C20-OH) DRIAAQEFINWLIAGGPSSGAPPPS-NH$_2$ |
| 5# | H-YAibEGTFTSDYSIYK(OEG-OEG-yGlu-C20-OH) DKIAAQEFINWLLAGGPSSGAPPPS-NH$_2$ |

TABLE 3-continued

| Compounds of the present disclosure | |
| --- | --- |
| Com-pound No. | Molecular structure |
| 6# | H-YAibEGTFTSDYSIYK(OEG-OEG-yGlu-C20-OH)DRIAAQEFVNWLLAGGPSSGAPPPS-NH$_2$ |
| 7# | H-YAibEGTFTSDYSIYK(OEG-OEG-yGlu-C20-OH)DKIAAQEFVNWLLAGGPSSGAPPPS-NH$_2$ |
| 8# | H-YAibEGTFTSDYSIYLEK(OEG-OEG-yGlu-C20-OH)IAAQEFVNWLLAGGPSSGAPPPS-NH$_2$ |
| 9# | H-YAibEGTFTSDYSIYLEK(OEG-OEG-yGlu-C20-OH)IAAQEFVNWLIAGGPSSGAPPPS-NH$_2$ |
| 10# | H-YAibEGTFTSDYSIYLEK(OEG-OEG-yGlu-C20-OH)IAAQEFINWLIAGGPSSGAPPPS-NH$_2$ |
| 11# | H-YAibEGTFTSDYSIYLEK(OEG-OEG-yGlu-C20-OH)IAAQEFINWLLAGGPSSGAPPPS-NH$_2$ |
| 12# | H-YAibEGTFTSDYSIYK(OEG-OEG-yGlu-C20-OH)EKIAAQEFVNWLIAGGPSSGAPPPS-NH$_2$ |
| 13# | H-YAibEGTFTSDYSIYK(OEG-OEG-yGlu-C20-OH)ERIAAQEFVNWLIAGGPSSGAPPPS-NH$_2$ |
| 14# | H-YAibEGTFTSDYSIYK(OEG-OEG-yGlu-C20-OH)EKIAAQEFINWLIAGGPSSGAPPPS-NH$_2$ |
| 15# | H-YAibEGTFTSDYSIYK(OEG-OEG-yGlu-C20-OH)ERIAAQEFINWLIAGGPSSGAPPPS-NH$_2$ |
| 16# | H-YAibEGTFTSDYSIYK(OEG-OEG-yGlu-C20-OH)EKIAAQEFINWLLAGGPSSGAPPPS-NH$_2$ |
| 17# | H-YAibEGTFTSDYSIYK(OEG-OEG-yGlu-C20-OH)ERIAAQEFVNWLLAGGPSSGAPPPS-NH$_2$ |

The purity of the compounds was determined by a combination of analytical high performance liquid chromatography and ultra performance liquid chromatography/mass spectrometry, with the purity of some of the compounds shown in Table 4 below.

TABLE 4

| Combination of analytical high performance liquid chromatography and liquid chromatography/mass spectrometry for determining the purity and molecular weight of compounds 8#-11# | |
| --- | --- |
| Compound No. | Purity |
| 8# | 96.30% |
| 9# | 93.28% |
| 10# | 94.56% |
| 11# | 92.18% |

Biological Evaluation

The present disclosure is further described and explained below with reference to test examples, but these examples are not intended to limit the scope of the present disclosure.

1. Experimental Reagent

TABLE 5

| Reagents used in this experiment and sources | | |
| --- | --- | --- |
| No. | Reagent | Source |
| 1 | DMEM/F12 | Gibco 11330032 |
| 2 | Casein | Sigma C3400-500G |
| 3 | 3-Isobutyl-1-methylxanthine | Sigma I7018-250MG |
| 4 | cAMP - Gs Dynamic kit - 20,000 tests | Cisbio 62AM4PEC |
| 5 | Corning ® 384 well microplate, low volume | Sigma CLS4514-50EA |
| 6 | 96-well V-bottom plate (PS) | Axygen WIPP02280 |
| 7 | Countess ® Cell Counting Chamber Slides | Invitrogen C10228 |
| 8 | puromycin | ThermoFisher A1113803 |
| 9 | Hygromycin B | Sigma A1720 |
| 10 | PBS | Gibco 10010023 |
| 11 | 0.25% Trypsin-EDTA(1X), Phenol Red | ThermoFisher 25200-114 |
| 12 | Gibco ™ Fetal Bovine Serum, Qualified, Australia Origin | ThermoFisher 10099-141 |
| 13 | Glucose | Sigma G8270-100G |

2. Experimental Instruments

TABLE 6

| Instrument used in this experiment and sources | | |
| --- | --- | --- |
| No. | Instrument | Source |
| 1 | CO$_2$ incubator | Thermo 311 |
| 2 | Biosafety cabinet | BOXUN BSC-1300IIA2 |
| 3 | Refrigerated centrifuge | Eppendorf 5702R |
| 4 | Haier double-door household refrigerator | HaierBCD-268TN |
| 5 | Cell counter | Life Technologies Countess II |
| 6 | Medicine storage box | Haier hyc-940 |
| 7 | Refrigerator at −20° C. | HaierDW-25L262 |
| 8 | Refrigerated centrifuge 5810R | Eppendorf 5810R |
| 9 | Automatic dispenser (Multidrop) | Thermo 5840300 |
| 10 | Microplate reader | BioTek H1MFD |
| 11 | CO$_2$ bacteria incubator | BOXUN BC-J80S |
| 12 | Active glucometer | Roche |

Example 3. Evaluation of Agonist Activity of Compounds of the Present Disclosure Against Glucagon-Like Peptide-1 Receptor (GLP-1R)

1. Experimental Objective

This test example was intended to determine agonist activity of the compounds of the present disclosure against the glucagon-like peptide-1 receptor (GLP-1R).

2. Experimental Procedures

Cryopreserved CHO-K1/GLP-1R/CRE-luc stable cell strains (which can be prepared by conventional methods in the art) were taken out of a liquid nitrogen tank, rapidly thawed in a water bath at 37° C., resuspended in a DMEM/F12 medium (Gibco Cat #11330032), and centrifuged, and the cells were washed once, resuspended in an assay buffer, i.e., DMEM/F12 medium containing 0.1% casein (Sigma Cat # C3400), adjusted for cell density with the assay buffer, and seeded in a 384-well plate (Sigma Cat # CLS4514) at a density of 2500 cells/5 µL/well. Then 2.5 µL of an IBMX working solution (Sigma Cat #17018) prepared in a buffer (the final concentration of IBMX was 0.5 mM) and 2.5 µL of polypeptide samples diluted in a gradient were added to each well, and the plate was centrifuged at 1000 rpm for 1 min, shaken for 30 s for mixing well, and left to stand for incubation at room temperature for 30 min. Detection was performed using the Cisbio cAMP-Gs Dynamic kit (Cisbio Cat #62AM4PEC), and cAMP-d2 and Anti-cAMP-$Eu^{3+}$-Cryptate were separately diluted in a 20-fold gradient and mixed well with cAMP Lysis & Detection Buffer. 5 µL of diluted cAMP-d2 solution was added to each well, followed by the addition of 5 µL of diluted Anti-cAMP-Eu'-Cryptate solution, and the mixture was shaken for 30 s for mixing well, and incubated at room temperature for 1 h away from light.

3. Data Processing

HTRF signal reading was performed using a Biotek Synergy H1 microplate reader at an excitation wavelength of 320 nm and emission wavelengths of 620 nm and 665 nm. The signal ratio (665 nm/620 nm×10,000) was calculated and fitted non-linearly to sample concentrations in GraphPad Prism 6 using a four-parameter equation to obtain $EC_{50}$ values, with the specific data shown in Table 7 below.

Example 4. Evaluation of Agonist Activity of Compounds of the Present Disclosure Against Glucose-Dependent Insulinotropic Polypeptide Receptor (GIP Receptor)

1. Experimental Objective

This example was intended to determine agonist activity of the compounds of the present disclosure against the glucose-dependent insulinotropic polypeptide receptor (GIP receptor).

2. Experimental Procedures

Wild-type CHO-K1 cells were collected, and the cell suspension was adjusted to an appropriate density, seeded in a 6-well plate at 2 mL/well, and placed in an incubator at 37° C. with 5% CO2 for adherence culture overnight. The transfection mixture (hGIP receptor plasmid, Fugene HD (Promega Cat # E2311), and OptiMEM (Gibco Cat #31985070)) was mixed well and left to stand at room temperature for 15 min, added to the corresponding cell wells in a volume of 100 µL, and transfected for 24 h to enable the overexpression of the hGIP receptor on the surface of CHO-K1 cells. After the transient transfection was completed, the cells in the 6-well plate were collected, washed once with an assay buffer, i.e., DMEM/F12 medium (Gibco Cat #11330032) containing 0.1% casein (Sigma Cat # C3400), adjusted for cell density using the assay buffer, and seeded in a 384-well plate (Sigma Cat # CLS4514) at a density of 5000 cells/5 µL/well. Then 2.5 µL of an IBMX working solution (Sigma Cat #17018) prepared in a buffer (the final concentration of IBMX was 0.5 mM) and 2.5 µL of polypeptide samples diluted in a gradient were added to each well, and the plate was centrifuged at 1000 rpm for 1 min, shaken for 30 s for mixing well, and left to stand for incubation at room temperature for 30 min. Detection was performed using the Cisbio cAMP-Gs Dynamic kit (Cisbio Cat #62 AM4PEC), and cAMP-d2 and Anti-cAMP-$Eu^{3+}$-

30

Cryptate were separately diluted in a 20-fold gradient and mixed well with cAMP Lysis & Detection Buffer. 5 µL of diluted cAMP-d2 solution was added to each well, followed by the addition of 5 µL of diluted Anti-cAMP-$Eu^{3+}$-Cryptate solution, and the mixture was shaken for 30 s for mixing well, and incubated at room temperature for 1 h away from light.

3. Data Processing

HTRF signal reading was performed using a Biotek Synergy H1 microplate reader at an excitation wavelength of 320 nm and emission wavelengths of 620 nm and 665 nm. The signal ratio (665 nm/620 nm×10,000) was calculated and fitted non-linearly to sample concentrations in GraphPad Prism 6 using a four-parameter equation to obtain $EC_{50}$ values, with the specific values shown in Tables 7 and 8 below.

TABLE 7

| Determination results of agonist activity against human GLP-1R and human GIP receptor | | |
|---|---|---|
| Compound | Human GLP-1R activity ($EC_{50}$ nM) | Human GIP receptor activity ($EC_{50}$ nM) |
| Natural GLP-1 | 0.010 | N/A |
| Natural GIP | N/A | 0.011 |
| Semaglutide | 0.024 | >10 |
| LY3298176 | 0.13 | 0.056 |
| 7# | 0.021 | 0.11 |

TABLE 8

| Determination results of agonist activity against human GLP-1R and human GIP receptor | | |
|---|---|---|
| Compound | Human GLP-1R activity ($EC_{50}$ nM) | Human GIP receptor activity ($EC_{50}$ nM) |
| Natural GLP-1 | 0.006 | N/A |
| Natural GIP | N/A | 0.006 |
| Semaglutide | 0.014 | >10.0 |
| LY3298176 | 0.078 | 0.031 |
| 9# | 0.049 | 0.040 |
| 10# | 0.065 | 0.056 |
| 12# | 0.030 | 0.170 |
| 13# | 0.017 | 0.130 |
| 14# | 0.013 | 0.130 |
| 15# | 0.015 | 0.230 |
| 16# | 0.029 | 0.095 |
| 17# | 0.022 | 0.110 |
| 18# | 0.013 | 0.060 |

4. Experimental Conclusion

Through the design of the polypeptide skeleton and the subsequent site-directed fatty acid modification, the compounds of the present disclosure have stronger agonist activity against the GLP-1/GIP receptor than many GLP-1/GIP receptor dual-agonist polypeptides in the art, and thus have better potential for treating metabolic diseases. In addition, LY3298176 shows preferential activity against the GIP receptor, in contrast to compounds 12 #-18 # of the present disclosure, which show preferential activity against GLP-1R.

Example 5. Stability Test of Some of Compounds of the Present Disclosure

Stability in plasma is important for therapeutic polypeptide drugs, since the polypeptide drugs are likely to be sensitive to polypeptide hydrolases and protein hydrolases in plasma. The half-life and efficacy of polypeptides that are unstable in plasma will be affected.

1. Experimental Objective

This experiment was intended to test the stability of some of the compounds of the present disclosure in human plasma.

2. Experimental Procedures

5 μL of each of samples at concentrations of 20 ng/mL, 50 ng/mL, 100 ng/mL, 200 ng/mL, 500 ng/mL, 1000 ng/mL, 2000 ng/mL, 5000 ng/mL and 10000 ng/mL was added to 45 μL of human plasma. The content of the compounds in the samples was determined by the LC-MS method and a standard curve was formed. 5 μL of a 1 mg/mL polypeptide solution was added to 45 μL of human plasma. Five samples were prepared for each test compound, and the samples were taken at 0 min, 30 min, 60 min, 120 min and 240 min, respectively, and determined for the content of the retained compound by the LC-MS method. With the content at 0 min as the standard (100%), the relative content of the retained compounds in the samples at other time points was calculated. The LC-MS method for detecting the compounds was as follows: a 5% acetonitrile solution was prepared as solution A, a 95% acetonitrile solution was prepared as solution B, a solution gradient was formed at a flow rate of 0.6 mL/min according to the time points and solution proportions shown in Table 9, and 15 μL of the sample was injected and determined for the content of the compound using a Raptor Biphenyl 2.7 μm detection column, see Table 9.

TABLE 9

Test time points and solution proportions

| Time (min) | A (%) | B (%) |
| --- | --- | --- |
| 0.20 | 95.0 | 5.00 |
| 1.70 | 5.00 | 95.0 |
| 2.00 | 5.00 | 95.0 |
| 2.01 | 95.0 | 5.00 |
| 2.50 | 95.0 | 5.00 |

3. Experimental Results

The data for the stability of some of the compounds of the present disclosure in plasma are shown in Table 10 below.

TABLE 10

Test results of the stability of the compounds in plasma

| Compound | The relative content of compounds retained in plasma (%) | | | | |
| --- | --- | --- | --- | --- | --- |
| | 0 min | 30 min | 60 min | 120 min | 240 min |
| LY3298176 | 100.00 | 102.89 | 114.76 | 117.59 | 113.35 |
| 7# | 100.00 | 101.45 | 101.66 | 103.28 | 102.15 |

Conclusion

It was found by study that compound 7 # of the present disclosure has similar stability (relative content>90%) in human plasma compared to compound LY3298176 at the 4-h time point.

Example 6. Pharmacokinetic Properties of Some of Compounds of the Present Disclosure in Mice Plasma stability is one of the factors that affect the pharmacokinetics of polypeptide drugs. The pharmacokinetics of polypeptide drugs in vivo is also affected by factors such as absorption and clearance of the polypeptide drugs in vivo.

1. Experimental Objective

This experiment was intended to study the pharmacokinetic behavior of the compounds of the present disclosure in Balb/c mice (plasma) after a single intravenous injection by taking the mice as test animals.

2. Experimental Procedures

Seven- to nine-week-old male Balb/c mice weighing 18-30 g were purchased from Shanghai Jiesijie Laboratory Animal Co., Ltd. After compound 7 # was prepared in a buffer containing 20 mM citric acid (pH=7.0), compound 7 # was intravenous injected into mice at a dose of 30 nmol/kg body weight via tail vein, and 0.2 mL of blood was separately collected at time points of 0 h, 0.083 h, 0.25 h, 0.5 h, 1 h, 2 h, 4 h, 6 h, 8 h, 24 h, and 32 h. The collected blood of mice was centrifuged at 6000 rpm for 6 min at 4° C. to separate the plasma. The content of compound 7 # in plasma of mice was assayed by the experimental procedures of Example 3.3.

3. Experimental Results

Through the above experimental procedures, the specific data are shown in Table 11 below.

TABLE 11

Pharmacokinetic behavior of a single intravenous injection in mice (plasma)

| PK parameters | Unit | Compound 7# |
| --- | --- | --- |
| $T_{1/2}$ | h | 13.0 |
| $AUC_{Inf}$ | h*ng/mL | 16133 |

4. Experimental Conclusion

It was found by study that compound 7 # of the present disclosure has good pharmacokinetic properties after intravenous injection into mice, indicating that this compound is advantageous in treating diseases, for example, it can support subcutaneous injection once a week in humans.

Example 7. Pharmacokinetic Properties of Some of Compounds of the Present Disclosure in Mice

1. Experimental Objective

This experiment was intended to study the pharmacokinetic behavior of the compounds of the present disclosure in Balb/c mice (plasma) after a single subcutaneous injection by taking the mice as test animals.

2. Experimental Procedures

Seven- to nine-week-old male Balb/c mice weighing 18-30 g were purchased from Shanghai Jiesijie Laboratory Animal Co., Ltd. After compound 7 # was prepared in a buffer containing 20 mM citric acid (pH=7.0), compound 7 # was subcutaneously injected into mice at a dose of 30 nmol/kg body weight via left side of abdomen, and 0.2 mL of blood was separately collected at time points of 0 h, 0.083 h, 0.25 h, 0.5 h, 1 h, 2 h, 4 h, 6 h, 8 h, 24 h, and 32 h. The collected blood of mice was centrifuged at 6000 rpm for 6 min at 4° C. to separate the plasma. The content of compound 7 # in plasma of mice was assayed by the experimental procedures of Example 5.2.

3. Experimental Results

Through the above experimental procedures, the specific data are shown in Table 12 below.

immobilized with the tail exposed, and a little was cut off the tail, then the tail was squeezed to bleed, and blood glucose was determined using a Roche active glucometer after the 1st drop of blood was discarded. The area under the blood glucose curve (AUC) was calculated from the results of all points.

3. Experimental Results

Through the above experimental procedures, the specific data are shown in Table 13 below.

TABLE 13

| Change in blood glucose values of mice after a single subcutaneous administration | | | | | | | |
|---|---|---|---|---|---|---|---|
| Test | | Blood glucose (mmol/L, mean ± SD) | | | | | AUC |
| compounds | Dose | 0 min | 15 min | 30 min | 60 min | 120 min | (mmol/L · hr) |
| Placebo | — | 5.3 ± 0.6 | 20.5 ± 2.0 | 24.0 ± 1.4 | 19 ± 1.3 | 10.9 ± 1.2 | 34.5 ± 2.4 |
| 7# | 10 nmol/kg | 4.4 ± 0.8 | 6.7 ± 0.8 | 6.2 ± 1.3 | 5.7 ± 1.2 | 3.8 ± 1.1 | 10.7 ± 1.8 |
| LY3298176 | 10 nmol/kg | 3.2 ± 0.2 | 9.1 ± 1.3 | 8 ± 1.4 | 6.4 ± 1.0 | 4.5 ± 0.7 | 12.7 ± 1.6 |

4. Experimental Conclusion

In this experiment, compound 7 # of the present disclosure shows significant blood glucose-lowering effect on normal mice at a dose of 10 nmol/kg body weight, with the area under the blood glucose curve of compound 7 # group reduced by more than 60% compared to that of placebo (i.e., blank vehicle).

TABLE 12

| Pharmacokinetic results for compound 7# in mice | | |
|---|---|---|
| PK parameters | Unit | Compound 7# |
| $T_{1/2}$ | h | 10.1 |
| $AUC_{Inf}$ | h*ng/mL | 14488 |

4. Experimental Conclusion

It was found by study that the compound of the present disclosure has good pharmacokinetic properties after subcutaneous injection into mice, indicating that this compound is advantageous in treating diseases, for example, it can support subcutaneous injection once a week in humans.

Example 8. In Vivo Efficacy of Some of Compounds of the Present Disclosure

1. Experimental Objective

This experiment was intended to test the regulatory effect of some of the compounds of the present disclosure and compound LY3298176 on blood glucose in normal mice after a single subcutaneous injection.

2. Experimental Procedures

Ten- to twelve-week-old male C57BL/6 mice were purchased from Shanghai Jiesijie Laboratory Animal Co., Ltd. The C57BL/6 mice were subcutaneously injected with compound 7 # or compound LY3298176 (dose: 10 nmol/kg body weight) and a control buffer, and then fasted without water deprivation. 18 h later, a glucose solution at a concentration of 0.2 g/mL was intraperitoneally injected. Blood glucose values were measured by collecting blood from the tail of mice at time points of 0 min, 15 min, 30 min, 60 min, and 120 min according to the experimental design. The specific procedures were as follows: the mouse was physically

Example 9. Body Weight-Reducing Efficacy of Some of Compounds of the Present Disclosure

1. Experimental Objective

This experiment was intended to test the regulatory effect of the numbered compounds on the body weight of diet-induced obese mice after subcutaneous administration.

2. Experimental Procedures

High-fat food-induced obese male C57BL/6 mice (weighing 35-55 g, aged 10-12 weeks, purchased from Shanghai Jiesijie Laboratory Animal Co., Ltd.) were tested. The diet-induced obese C57BL/6 mice were separately subcutaneously injected with compound LY3298176 (10 nmol/kg body weight), compound 7 # (10 nmol/kg body weight), and compound 18 # (three doses of 3 nmol/kg, 10 nmol/kg and 100 nmol/kg body weight, administered once every 3 days). According to the experimental design, the body weight of each mouse was measured and recorded on day 0, day 3, day 6 and so on to day 27, the average body weight of each group of mice was calculated, and weight change curves were plotted by taking the body weight on the first day as the standard. At the end, the fat and other visceral organs of each part of the mice were taken out and weighed, and the viscera/brain ratio for fat in each part of each mouse was calculated. The effect of the drug on the fat was determined by comparing the change in the organ/brain ratio for fat of different parts of each group of mice.

3. Experimental Results

Through the above experimental procedures, the specific data are shown in Tables 14 to 16 below and FIG. 1.

TABLE 14

| | | Body Weight-Reducing Effect of Compounds on Induced Obese Mice | | | | | | | | | |
|---|---|---|---|---|---|---|---|---|---|---|---|
| Test | | Changes in body weight (%, mean ± SD) | | | | | | | | | |
| compounds | Dose | Day 1 | Day 4 | Day 7 | Day 10 | Day 13 | Day 16 | Day 19 | Day 22 | Day 25 | Day 28 |
| Placebo | — | 0 | −0.9 ± 1.6 | −2.6 ± 1.5 | −3.0 ± 2.4 | −3.5 ± 3.7 | −2.7 ± 4.8 | −2.8 ± 6.7 | −2.5 ± 8.4 | −1.4 ± 8.9 | −2.1 ± 9.6 |
| 7# | 10 nmol/kg | 0 | −11.0 ± 1.0 | −17.6 ± 2.6 | −22.6 ± 5.9 | −22.3 ± 6.3 | −22.7 ± 6.9 | −25.9 ± 6.2 | −23.9 ± 5.6 | −23.9 ± 5.6 | −25.5 ± 5.3 |

TABLE 15

| | Effect of compounds on rate of change in body weight (%, X ± s, n = 7/8) in diet-induced obese mice | | | | | |
|---|---|---|---|---|---|---|
| | Before administration | Days after administration | | | | |
| Groups | 0 | 1 | 2 | 3 | 4 | 5 |
| Normal control | 0 | 0.7 ± 3.1 | 1.6 ± 2.5 | 2.9 ± 1.9 | 0.7 ± 2 | −0.3 ± 1.8 |
| Model control | 0 | 0.7 ± 0.4 | 0.3 ± 0.9 | 1 ± 0.4 | 0.9 ± 0.9 | 1.4 ± 1 |
| LY3298176 (10 nmol/kg) | 0 | −4.2 ± 1 | −5.4 ± 0.8 | −4.4 ± 1.2 | −7.8 ± 1.6** | −8.7 ± 2.1** |
| 18# (3 nmol/kg) | 0 | −5 ± 0.6 | −6.3 ± 1 | −5.8 ± 1.9 | −9.1 ± 2.1** | −10.3 ± 3.2*** |
| 18# (10 nmol/kg) | 0 | −6.2 ± 1.1 | −8.6 ± 0.9** | −9.4 ± 1.6*** | −12.7 ± 2.4*** | −14.5 ± 3.3*** |
| 18# (100 nmol/kg) | 0 | −6.3 ± 0.5 | −10.9 ± 0.8*** | −13.2 ± 1*** | −15.7 ± 0.9*** | −19.2 ± 1.3*** |

| | Days after administration | | | | |
|---|---|---|---|---|---|
| Groups | 6 | 7 | 8 | 9 | 10 |
| Normal control | 1.2 ± 2.3 | 1.1 ± 1.5 | 1.2 ± 2.5 | −0.1 ± 2.4 | −0.3 ± 2.7 |
| Model control | 1.6 ± 0.9 | 2.5 ± 1.8 | 1.8 ± 1.3 | 1.7 ± 0.7 | 2.3 ± 1 |
| LY3298176 (10 nmol/kg) | −7.6 ± 2.8** | −10.4 ± 2.6*** | −10.7 ± 3.2*** | −9.6 ± 3.4*** | −12.3 ± 3.6*** |
| 18# (3 nmol/kg) | −10 ± 4.4*** | −13 ± 5.3*** | −13.9 ± 6.1*** | −13.9 ± 7.4*** | −16.6 ± 7.8*** |
| 18# (10 nmol/kg) | −15 ± 5.3*** | −18.3 ± 6.3*** | −20.1 ± 8*** | −20.3 ± 9.3*** | −23.4 ± 9.8*** |
| 18# (100 nmol/kg) | −21.8 ± 2.3*** | −24.7 ± 3.3*** | −27.6 ± 3.7*** | −29.6 ± 4.7*** | −31.6 ± 5.3*** |

| | Days after administration | | | |
|---|---|---|---|---|
| Groups | 11 | 12 | 13 | 14 |
| Normal control | 0 ± 2 | −0.2 ± 1.8 | 0.5 ± 1.9 | 2.2 ± 1.6 |
| Model control | 3.2 ± 1.8 | 2.7 ± 1.8 | 3.1 ± 1.2 | 3.3 ± 1 |
| LY3298176 (10 nmol/kg) | −12.4 ± 3.9*** | −11.1 ± 4*** | −13.5 ± 4.7*** | −13.1 ± 5.3*** |
| 18# (3 nmol/kg) | −16.4 ± 8.2*** | −15.7 ± 8.6*** | −18.2 ± 8.2*** | −17.1 ± 7.2*** |
| 18# (10 nmol/kg) | −23.9 ± 10.7*** | −23.5 ± 11.4*** | −26.4 ± 11.8*** | −25.1 ± 12.1*** |
| 18# (100 nmol/kg) | −33.7 ± 6.3*** | −34.4 ± 7.1*** | −35.6 ± 6.2*** | −36.7 ± 5.7*** |

| | Days after administration | | | | | | |
|---|---|---|---|---|---|---|---|
| Groups | 15 | 16 | 17 | 18 | 19 | 20 | 21 |
| Normal control | 2.6 ± 2 | 1.7 ± 1.6 | 1.2 ± 1.7 | 1.8 ± 1.1 | 1.1 ± 0.9 | 2 ± 2.1 | 2.9 ± 1.2 |
| Model control | 3.6 ± 1 | 3.5 ± 1.4 | 4.1 ± 1.4 | 2.8 ± 1.6 | 3.2 ± 2 | 3.2 ± 2.6 | 3.7 ± 2.6 |
| LY3298176 (10 nmol/kg) | −11.3 ± 5.5*** | −14.3 ± 6*** | −14.2 ± 6.6*** | −12.8 ± 6.6*** | −16.3 ± 6.2*** | −15.7 ± 6.6*** | −13.8 ± 6.6*** |
| 18# (3 nmol/kg) | −15.7 ± 7.4*** | −18.6 ± 7*** | −18.3 ± 7*** | −17.9 ± 7.1*** | −20.5 ± 7.5*** | −19.8 ± 7.4*** | −17.8 ± 7.3*** |

TABLE 15-continued

Effect of compounds on rate of change in body weight (%, X ± s, n = 7/8) in diet-induced obese mice

| | | | | | | | |
|---|---|---|---|---|---|---|---|
| 18# (10 nmol/kg) | −23.4 ± 9*** | −26.6 ± 9.7*** | −25.7 ± 8.7*** | −24.6 ± 8.2*** | −27.5 ± 7.6*** | −27.3 ± 7.2*** | −24.8 ± 6.7*** |
| 18# (100 nmol/kg) | −35.7 ± 5.6*** | *** | −38.2 ± 6.2*** | −37.8 ± 6.5*** | −38.5 ± 6.5*** | −39 ± 6.5*** | −37.4 ± 6.6*** |

| | Days after administration | | | | | | |
|---|---|---|---|---|---|---|---|
| Groups | 22 | 23 | 24 | 25 | 26 | 27 | 28 |
| Normal control | 2.3 ± 1.7 | 2.9 ± 1.9 | 2.8 ± 1.3 | 3.2 ± 2.1 | 3.7 ± 1.6 | 4.3 ± 2.1 | 5.1 ± 1.9 |
| Model control | 4 ± 2.5 | 4.3 ± 2.7 | 5 ± 2.9 | 5.2 ± 2.7 | 5.2 ± 2.9 | 5.9 ± 3.7 | 6.6 ± 3.3 |
| LY3298176 (10 nmol/kg) | −16.1 ± 6.8*** | −15.6 ± 7.1*** | −14.1 ± 7.1*** | −16.9 ± 7.2*** | −16 ± 7.7*** | −13.4 ± 7.8*** | −15.8 ± 7.6*** |
| 18# (3 nmol/kg) | −19.3 ± 8.2*** | −19.1 ± 7.6*** | −17.3 ± 7.4*** | −19.9 ± 7.6*** | −18.8 ± 8*** | −16.1 ± 7.6*** | −19.2 ± 8*** |
| 18# (10 nmol/kg) | −28.1 ± 7.4*** | −27.1 ± 7*** | −26 ± 7.1*** | −28.5 ± 8.8*** | −27.8 ± 8.3*** | −24.8 ± 8.4*** | −28.2 ± 8.3*** |
| 18# (100 nmol/kg) | −38.3 ± 6.2*** | −38 ± 5.9*** | −36.8 ± 5.8*** | −38.6 ± 5.7*** | −38.9 ± 6*** | −36.8 ± 5.3*** | −37.9 ± 5.7*** |

**P < 0.01;
***P < 0.001, compared to model control group

TABLE 16

Compounds on the change of the viscera/brain ratio (%, X ± s, n = 7-8) for fat mass in different parts of diet-induced obese mice

| Groups | Scapular fat | Subcutaneous fat | Inguinal fat | Mesenteric fat | Perirenal fat | Epididymal fat |
|---|---|---|---|---|---|---|
| Model control | 51.6 ± 31.8 | 320.2 ± 54.2 | 510.2 ± 104.3 | 220.3 ± 68.6 | 306.2 ± 67.7 | 384.1 ± 61.1 |
| LY3298176 (10 nmol/kg) | 52 ± 26 | 144.6 ± 75.8*** | 289.1 ± 169.2** | 105.3 ± 93** | 163.2 ± 57.9*** | 316.0 ± 75.6 |
| 18# (3 nmol/kg) | 48 ± 15.3 | 120 ± 62*** | 281.5 ± 140.1** | 84.8 ± 41.3*** | 159.2 ± 87.6*** | 254.6 ± 113.4* |
| 18# (10 nmol/kg) | 42.5 ± 17 | 122 ± 73.2*** | 194.4 ± 86.2*** | 53.3 ± 14.6*** | 109.4 ± 57.1*** | 211.7 ± 80.7** |
| 18# (100 nmol/kg) | 32.3 ± 7 | 57.1 ± 21.2*** | 92 ± 34.5*** | 27.4 ± 11.1*** | 46.6 ± 18.2*** | 102.9 ± 32.2*** |

*P < 0.05;
**P < 0.01;
***P < 0.001, compared to model control group

4. Experimental Conclusion

In this experiment, at the doses of 3 nmol/kg, 10 nmol/kg and 100 nmol/kg, the compounds 7 # and 18 # of the present disclosure show significant body weight-reducing effect on high-fat food-induced obese mice and exhibit significant dose dependence. The body weight of mice in 10 nmol/kg dose test group of the compound 18 # is reduced by more than 20.0% on day 27, in contrast, the body weight of mice in the same dose test group of the control compound LY3298176 is reduced by about 13.4%. In addition, the content of fat of each part (except scapular fat) of mice in all dose test groups of the compound 18 # is significantly reduced relative to that of the placebo (i.e., vehicle blank) group.

Figure 2:
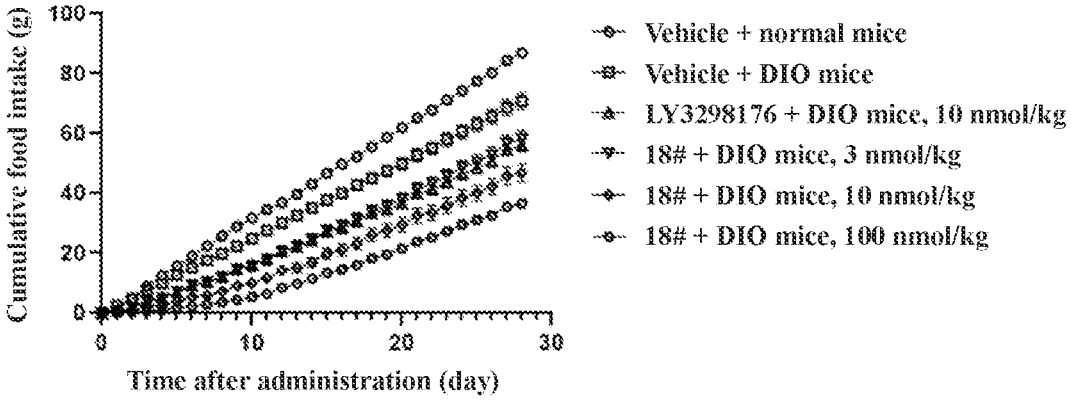
FIG. 2 shows the effect of the compound of the present disclosure on daily food intake ration of diet-induced obese mice.

Example 10. Effect of Compounds of the Present Disclosure on Food Intake Ration of Mice The food intake ration of mice in each group was measured daily during the test. The results are shown in Table 17 and FIG. 2.

The average daily food intake ration of DIO (diet-induced obesity) mice in the model control group was 2.5 g throughout the experiment. After subcutaneous injection of the compound 18 # or compound LY3298176 at different doses, the food intake ration of mice in all groups was reduced to different extents.

On the first day after the administration, the food intake ration of mice in each administration group was significantly reduced, with the food intake ration of mice in 3 nmol/kg, 10 nmol/kg and 100 nmol/kg dose groups of the compound 18 # being 0.6 g, 0.3 g and 0.2 g, respectively, which was significantly different from that of the model control group (2.5 g) and showed a better dose-effect relationship.

The cumulative food intake ration of the mice in the model control group within 5 days after the administration was 12.8 g, while the cumulative food intake ration of the mice in the 3 nmol/kg, 10 nmol/kg and 100 nmol/kg dose groups of the compound 18 # within 5 days after the administration was 7.2 g, 3.9 g and 1.8 g, respectively, which was significantly lower than that of the model control group and showed a better dose-effect relationship.

Daily food intake ration of mice in each administration group began to decrease on day 1 and resumed on days 2 and 3 after each administration. Daily feed intake ration showed an overall upward recovery trend during the administration. 28 days after the administration, the cumulative food intake ration of three dose groups of the compound 18 # was 58.2 g, 46.8 g and 36.7 g, respectively, which was significantly lower than that of the model control group (70.8 g) and showed a better dose dependence. Therefore, the compound 18 # can significantly reduce food intake ration of DIO mice.

TABLE 17

Effect of long-term administration of compound 18# on daily food intake ration of DIO mice (g, X ± s, n = 7-8)

| Groups | Days after administration | | | | | | |
|---|---|---|---|---|---|---|---|
| | 1 | 2 | 3 | 4 | 5 | 6 | 7 |
| Normal control | 1 ± 1.4 | 4 ± 0.5 | 4.1 ± 0.5 | 3.6 ± 0.8 | 3.2 ± 1 | 3.3 ± 0.5 | 3.4 ± 0.4 |
| Model control | 2.5 ± 0.4 | 2.4 ± 0.4 | 2.6 ± 0.3 | 2.3 ± 0.3 | 2.8 ± 0.3 | 2.4 ± 0.5 | 2.4 ± 0.3 |
| LY3298176 (10 nmol/kg) | 0.8 ± 0.2*** | 1.2 ± 0.2*** | 2.3 ± 0.3 | 0.9 ± 0.3*** | 1.8 ± 0.3*** | 2.3 ± 0.3 | 1.2 ± 0.3*** |
| Compound 18# (3 nmol/kg) | 0.6 ± 0.1*** | 1.3 ± 0.5*** | 2 ± 0.5 | 1.1 ± 0.4*** | 2.2 ± 1.3 | 2.1 ± 1.1 | 1.1 ± 0.6*** |
| Compound 18# (10 nmol/kg) | 0.3 ± 0.2*** | 0.6 ± 0.6*** | 1.1 ± 0.7*** | 0.7 ± 0.5*** | 1.1 ± 0.5*** | 1.5 ± 0.8** | 0.8 ± 0.4*** |
| Compound 18# (100 nmol/kg) | 0.2 ± 0.1*** | 0.1 ± 0.1*** | 0.4 ± 0.1*** | 0.4 ± 0.2*** | 0.6 ± 0.2*** | 0.7 ± 0.3*** | 0.5 ± 0.2*** |

| Groups | Days after administration | | | | | | |
|---|---|---|---|---|---|---|---|
| | 8 | 9 | 10 | 11 | 12 | 13 | 14 |
| Normal control | 3.3 ± 0.4 | 3.3 ± 0.7 | 2.8 ± 0.4 | 2.9 ± 1.1 | 2.2 ± 1.1 | 2.8 ± 0.3 | 3.4 ± 0.5 |
| Model control | 2.3 ± 0.3 | 2.5 ± 0.4 | 2.5 ± 0.4 | 2.8 ± 0.4 | 2.4 ± 0.3 | 2.6 ± 0.5 | 2.5 ± 0.3 |
| LY3298176 (10 nmol/kg) | 1.7 ± 0.4 | 2.7 ± 0.3 | 1.2 ± 0.4*** | 2 ± 0.3* | 2.8 ± 0.4 | 1.4 ± 0.6*** | 2 ± 0.5 |
| Compound 18# (3 nmol/kg) | 1.6 ± 0.6* | 2.5 ± 0.9 | 1.3 ± 0.6*** | 2 ± 0.3* | 3 ± 1 | 1.8 ± 1* | 2.3 ± 1 |
| Compound 18# (10 nmol/kg) | 1.1 ± 0.7*** | 2 ± 0.6 | 0.9 ± 0.4*** | 1.8 ± 0.8** | 2.4 ± 0.6 | 0.9 ± 0.4*** | 1.7 ± 0.7* |
| Compound 18# (100 nmol/kg) | 0.7 ± 0.5*** | 0.9 ± 0.6*** | 0.9 ± 0.6*** | 1.1 ± 0.5*** | 2 ± 1 | 1.3 ± 0.7*** | 1.7 ± 0.5* |

| Groups | Days after administration | | | | | | |
|---|---|---|---|---|---|---|---|
| | 15 | 16 | 17 | 18 | 19 | 20 | 21 | 22 |
| Normal control | 3.7 ± 0.7 | 3 ± 0.4 | 2.6 ± 0.2 | 3.3 ± 0.3 | 3.1 ± 0.3 | 3.3 ± 0.5 | 3.3 ± 0.2 | 2.7 ± 0.4 |
| Model control | 2.7 ± 0.3 | 2.1 ± 0.2 | 2.7 ± 0.2 | 2.3 ± 0.4 | 2.5 ± 0.5 | 2.4 ± 0.3 | 2.9 ± 0.3 | 2.3 ± 0.2 |
| LY3298176 (10 nmol/kg) | 3 ± 0.6 | 1.2 ± 0.4** | 2.1 ± 0.4 | 2.9 ± 1.1 | 1.2 ± 0.8*** | 2 ± 0.4 | 3.3 ± 0.3 | 1.4 ± 0.4** |
| Compound 18# (3 nmol/kg) | 2.9 ± 0.7 | 1.5 ± 0.7 | 2.2 ± 0.5 | 2.7 ± 0.3 | 1.7 ± 0.5* | 2.2 ± 0.5 | 3.4 ± 0.4 | 1.8 ± 0.5 |
| Compound 18# (10 nmol/kg) | 3 ± 0.9 | 1.2 ± 1** | 2.1 ± 0.9 | 2.9 ± 0.8 | 1.3 ± 0.5*** | 2 ± 0.5 | 3.2 ± 0.6 | 1 ± 0.4*** |
| Compound 18# (100 nmol/kg) | 2 ± 0.4 | 1 ± 0.3** | 1.6 ± 0.3** | 2 ± 0.4 | 1.4 ± 0.2** | 1.8 ± 0.3 | 2.4 ± 0.3 | 1.4 ± 0.5** |

| Groups | Days after administration | | | | | |
|---|---|---|---|---|---|---|
| | 23 | 24 | 25 | 26 | 27 | 28 |
| Normal control | 3.3 ± 0.3 | 3.1 ± 0.3 | 3.3 ± 0.8 | 2.8 ± 0.8 | 4.1 ± 0.3 | 2.5 ± 0.3 |
| Model control | 2.9 ± 0.4 | 2.6 ± 0.5 | 2.6 ± 0.3 | 2.4 ± 0.4 | 3 ± 0.5 | 2.1 ± 0.3 |
| LY3298176 (10 nmol/kg) | 2.5 ± 0.5 | 2.8 ± 0.4 | 1.8 ± 0.6 | 2.4 ± 0.4 | 3.9 ± 0.5 | 1.4 ± 0.3 |
| Compound 18# (3 nmol/kg) | 2.6 ± 0.4 | 2.9 ± 0.5 | 1.8 ± 0.8* | 2.5 ± 0.9 | 3.9 ± 0.5** | 1.3 ± 0.6* |
| Compound 18# (10 nmol/kg) | 2.3 ± 0.5 | 2.5 ± 0.6 | 1.6 ± 1.2** | 2.2 ± 0.8 | 3.6 ± 1 | 1 ± 0.5*** |
| Compound 18# (100 nmol/kg) | 2.1 ± 0.5* | 2.3 ± 0.4 | 1.5 ± 0.3*** | 1.6 ± 0.4* | 2.8 ± 0.3 | 1.2 ± 0.4* |

*P < 0.05;
**P < 0.01;
***P < 0.001, compared to model control group

Example 11. Improvement Effect of Some of Compounds of the Present Disclosure on Glucose Metabolism Level in db/db Mice

1. Experimental Objective

This experiment was intended to test the improvement effect of the numbered compounds on the glucose metabolism level in db/db mice after subcutaneous administration.

2. Experimental Procedures

C57BL/KsJ-db/db mice were separately subcutaneously injected with blank vehicle (20 mM sodium citrate+0.05% Tween-80, pH 7.5), compound LY3298176 (100 nmol/kg body weight), and compound 18 # (three doses of 10 nmol/kg body weight, 30 nmol/kg body weight and 100 nmol/kg body weight) on days 0, 3, 7, 10, 14, 17, 21, 24 and 27. Each administration group contained 10 db/db mice. According to the experimental design, tail vein blood was collected by needle pricking on days 0, 7, 14, 21 and 28 and determined for fasting blood glucose levels with a glucometer and glucose dipsticks, and the mice were fasted 6 h prior to the blood collection at each time point. Tail vein blood was collected by needle pricking on days 3, 10, 17, 24 and 27 and randomly determined for blood glucose levels with a glucometer. Finally, at the end of the experiment on day 28, all the animals in the administration groups were subjected to 2-5% isoflurane inhalation anesthesia, and 100 μL of EDTA-K2 anticoagulated whole blood was collected through the orbit of each mouse and used for the determination of glycated hemoglobin.

3. Experimental Results

Through the above experimental procedures, the specific data are shown in Tables 18 to 20 below.

TABLE 18

| Effect of long-term administration of compound 18# on fasting blood glucose of db/db mice | | | | | |
|---|---|---|---|---|---|
| Administration group | Concentration of fasting blood glucose (mmol/L, mean ± SD) | | | | |
| | Day 0 | Day 7 | Day 14 | Day 21 | Day 28 |
| Blank control | 14.25 ± 1.27 | 17.92 ± 1.33 | 22.89 ± 1.88 | 24.95 ± 1.52 | 25.94 ± 1.32 |
| LY3298176 (100 nmol/kg) | 14.35 ± 1.41 | 7.44 ± 0.76 | 7.56 ± 0.88 | 9.42 ± 1.67 | 9.89 ± 1.28*** |
| #18 (10 nmol/kg) | 14.77 ± 1.30 | 6.05 ± 0.42 | 6.30 ± 0.46 | 7.89 ± 0.81 | 9.41 ± 0.97*** |
| #18 (30 nmol/kg) | 14.13 ± 1.32 | 6.21 ± 0.26 | 6.40 ± 0.57 | 7.03 ± 0.52 | 9.68 ± 1.03*** |
| #18 (100 nmol/kg) | 14.67 ± 1.46 | 5.85 ± 0.33 | 6.25 ± 0.32 | 6.13 ± 0.19 | 7.89 ± 0.41*** |

***$p < 0.001$ vs. blank control group.

TABLE 19

| Effect of long-term administration of compound 18# on random blood glucose of db/db mice | | | | |
|---|---|---|---|---|
| Administration group | Concentration of random blood glucose (mmol/L, mean ± SD) | | | |
| | Day 0 | Day 10 | Day 17 | Day 24 |
| Blank control | 23.06 ± 0.97 | 26.40 ± 0.90 | 27.64 ± 1.15 | 30.22 ± 0.74 |
| LY3298176 (100 nmol/kg) | 18.60 ± 1.52 | 17.10 ± 1.96 | 17.98 ± 1.37 | 20.70 ± 1.27*** |
| #18 (10 nmol/kg) | 20.42 ± 1.56 | 20.66 ± 1.48 | 18.91 ± 1.33 | 21.17 ± 2.07** |
| #18 (30 nmol/kg) | 16.73 ± 1.59 | 15.88 ± 1.86 | 17.30 ± 1.17 | 17.43 ± 1.92*** |
| #18 (100 nmol/kg) | 9.11 ± 1.25 | 12.34 ± 1.12 | 11.89 ± 1.15 | 11.51 ± 0.95*** |

**$p < 0.01$ vs. blank control group;
***$p < 0.001$ vs. blank control group.

TABLE 20

| Effect of Long-term administration of compound 18# on the glycated hemoglobin level in db/db mice | |
|---|---|
| Administration group | Glycated hemoglobin (%, mean ± SD) |
| Blank control | 6.54 ± 0.17 |
| LY3298176 (100 nmol/kg) | 4.58 ± 0.23** |
| #18 (10 nmol/kg) | 4.71 ± 0.23*** |
| #18 (30 nmol/kg) | 4.53 ± 0.17*** |
| #18 (100 nmol/kg) | 3.78 ± 0.13*** |

**$p < 0.01$ vs. blank control group;
***$p < 0.001$ vs. blank control group.

4. Experimental Conclusion

In this experiment, at the doses of 10 nmol/kg, 30 nmol/kg and 100 nmol/kg, the compound 18 # of the present disclosure show excellent improvement effect on the glucose metabolism level in db/db mice and show significant dose dependence. The glycated hemoglobin level of the 100 nmol/kg dose group of the compound 18 # is 3.78% at the end of the experiment, in contrast, the glycated hemoglobin level of the same dose group of the control compound LY3298176 is 4.58%. Therefore, the efficacy of the compound 18 # in improving the glucose metabolism level in db/db mice is significantly better than that of the control compound LY3298176 at the same dose.

The invention claimed is:

1. A GLP-1 analog having general formula (I) or a pharmaceutically acceptable salt thereof:

(I)

(SEQ ID NO: 19)

$$R_1 - X_1 - X_2 - Glu - Gly - Thr - Phe - Thr - Ser - Asp - X_{10} -$$

$$Ser - X_{12} - X_{13} - X_{14} - X_{15} - X_{16} - X_{17} - X_{18} - X_{19} - X_{20} - Glu -$$

$$Phe - X_{23} - X_{24} - Trp - Leu - X_{27} - X_{28} - X_{29} - X_{30} - Pro - Ser -$$

$$Ser - Gly - Ala - Pro - Pro - Pro - Ser - R_2$$

wherein:

$R_1$ is H, alkyl, acetyl, formyl, benzoyl, trifluoroacetyl, pGlu or absent;

$R_2$ is —NH$_2$, —OH or absent;

$X_1$ is an amino acid residue of Tyr;

$X_2$ is an amino acid residue of Aib;

$X_{10}$ is an amino acid residue of Tyr;

$X_{12}$ is an amino acid residue of Ile;

$X_{13}$ is an amino acid residue of Tyr;

$X_{14}$ is Y1;

$X_{15}$ is selected from the group consisting of amino acid residues of Asp and Glu;

$X_{16}$ is selected from the group consisting of amino acid residues of Arg and Lys;

$X_{17}$ is an amino acid residue of Ile;

$X_{18}$ is an amino acid residue of Ala;

$X_{19}$ is an amino acid residue of Ala;

$X_{20}$ is an amino acid residue of Gln;

$X_{23}$ is selected from the group consisting of amino acid residues of Ile and Val;

$X_{24}$ is an amino acid residue of Asn;

$X_{27}$ is selected from the group consisting of amino acid residues of Ile and Leu;

$X_{28}$ is an amino acid residue of Ala;

$X_{29}$ is an amino acid residue of Gly;

$X_{30}$ is an amino acid residue of Gly;

Y1 is a Lys residue comprising a substituent on a side chain, the substituent having a structure of formula $\{[2\text{-}(2\text{-amino-ethoxy})\text{-ethoxy}]\text{-acetyl}\}_a\text{-}(\gamma\text{-Glu})_b\text{-CO-}(CH_2)_c\text{-COOH}$;

13122314v1 a is an integer of 1-3;

b is 1 or 2; and c is an integer of 10-30.

2. The GLP-1 analog according to claim 1, wherein the GLP-1 analog is:

-continued

14#

15#

16#

-continued

17#, or

18#, or a pharmaceutically acceptable salt thereof.

3. A pharmaceutical composition, comprising the GLP-1 analog of claim 2, and one or more pharmaceutically acceptable excipients or carriers.

4. The GLP-1 analog according to claim 1, wherein the GLP-1 analog is 7 #:

D-K-I-A-A-Q-E-F-V-N-W-L-L-A-G-G-P-S-S-G-A-P-P-P

Y-I-S-Y-D-S-T-F-T-G-E or a pharmaceutically acceptable salt thereof.

5. A pharmaceutical composition, comprising the GLP-1 analog of claim 4, and one or more pharmaceutically acceptable excipients or carriers.

6. The GLP-1 analog according to claim 1, wherein the GLP-1 analog is 12 #:

E-K-I-A-A-Q-E-F-V-N-W-L-L-A-G-G-P-S-S-G-A-P-P-P

Y-I-S-Y-D-S-T-F-T-G-E or a pharmaceutically acceptable salt thereof.

7. A pharmaceutical composition, comprising the GLP-1 analog of claim 6, and one or more pharmaceutically acceptable excipients or carriers.

8. The GLP-1 analog according to claim 1, wherein the GLP-1 analog is 13 #:

E-R-I-A-A-Q-E-F-V-N-W-L-L-A-G-G-P-S-S-G-A-P-P-P

Y-I-S-Y-D-S-T-F-T-G-E

H₃C—CH₃

N—Y—H or a pharmaceutically acceptable salt thereof.

9. A pharmaceutical composition, comprising the GLP-1 analog of claim 8, and one or more pharmaceutically acceptable excipients or carriers.

10. The GLP-1 analog according to claim 1, wherein the GLP-1 analog is 14 #:

E-K-I-A-A-Q-E-F-I-N-W-L-I-A-G-G-P-S-S-G-A-P-P-P

Y-I-S-Y-D-S-T-F-T-G-E

H₃C—CH₃

N—Y—H or a pharmaceutically acceptable salt thereof.

11. A pharmaceutical composition, comprising the GLP-1 analog of claim 10, and one or more pharmaceutically acceptable excipients or carriers.

12. The GLP-1 analog according to claim 1, wherein the GLP-1 analog is 15 #:

or a pharmaceutically acceptable salt thereof.

13. A pharmaceutical composition, comprising the GLP-1 analog of claim 12, and one or more pharmaceutically acceptable excipients or carriers.

14. The GLP-1 analog according to claim 1, wherein the GLP-1 analog is 16 #:

or a pharmaceutically acceptable salt thereof.

15. A pharmaceutical composition comprising the GLP-1 analog of claim 14, and one or more pharmaceutically acceptable carriers, diluents or excipients.

16. The GLP-1 analog according to claim 1, wherein the GLP-1 analog is 17 #:

or a pharmaceutically acceptable salt thereof.

17. A pharmaceutical composition comprising the GLP-1 analog of claim 16, and one or more pharmaceutically acceptable carriers, diluents or excipients.

18. The GLP-1 analog according to claim 1, wherein the GLP-1 analog is 18 #:

or a pharmaceutically acceptable salt thereof.

19. A pharmaceutical composition comprising the GLP-1 analog of claim 18, and one or more pharmaceutically acceptable carriers, diluents or excipients.

20. A pharmaceutical composition, comprising the GLP-1 analog of claim 1, and one or more pharmaceutically acceptable excipients or carriers.

21. A method of treating type II diabetes in a subject in need thereof, the method comprising administering to the subject in need thereof a GLP-1 analog or a pharmaceutically acceptable salt thereof, wherein the GLP-1 analog has general formula (I):

(SEQ ID NO: 19)

$R_1$-$X_1$-$X_2$-Glu-Gly-Thr-Phe-Thr-Ser-Asp-$X_{10}$-Ser-$X_{12}$-

$X_{13}$-$X_{14}$-$X_{15}$-$X_{16}$-$X_{17}$-$X_{18}$-$X_{19}$-$X_{20}$-Glu-Phe-$X_{23}$-$X_{24}$-Trp-

-continued

Leu-$X_{27}$-$X_{28}$-$X_{29}$-$X_{30}$-Pro-Ser-Ser-Gly-Ala-Pro-Pro-

Pro-Ser-$R_2$  (I)

wherein:

$R_1$ is H, alkyl, acetyl, formyl, benzoyl, trifluoroacetyl, pGlu or absent;

$R_2$ is —$NH_2$, —OH or absent;

$X_1$ is an amino acid residue of Tyr;

$X_2$ is an amino acid residue of Aib;

$X_{10}$ is an amino acid residue of Tyr;

$X_{12}$ is an amino acid residue of Ile;

$X_{13}$ is an amino acid residue of Tyr;

$X_{14}$ is Y1;

$X_{15}$ is selected from the group consisting of amino acid residues of Asp and Glu;

$X_{16}$ is selected from the group consisting of amino acid residues of Arg and Lys;

$X_{17}$ is an amino acid residue of Ile;

$X_{18}$ is an amino acid residue of Ala;

$X_{19}$ is an amino acid residue of Ala;

$X_{20}$ is an amino acid residue of Gln;

$X_{23}$ is selected from the group consisting of amino acid residues of Ile and Val;

$X_{24}$ is an amino acid residue of Asn;

$X_{27}$ is selected from the group consisting of amino acid residues of Ile and Leu;

$X_{28}$ is an amino acid residue of Ala;

$X_{29}$ is an amino acid residue of Gly;

$X_{30}$ is an amino acid residue of Gly;

Y1 is a Lys residue comprising a substituent on a side chain, the substituent having a structure of formula $\{[2\text{-}(2\text{-amino-ethoxy})\text{-ethoxy}]\text{-acetyl}\}_a\text{-}(\text{y-Glu})_b\text{-CO-}(CH_2)_c\text{-COOH}$;

a is an integer of 1-3;

b is 1 or 2; and c is an integer of 10-30.

22. The method of claim 21, wherein the GLP-1 analog is #:

or a pharmaceutically acceptable salt thereof.

23. The method of claim 21, wherein the GLP-1 analog is #:

or a pharmaceutically acceptable salt thereof.

24. The method of claim 21, wherein the GLP-1 analog is

13 #:

or a pharmaceutically acceptable salt thereof.

25. The method of claim 21, wherein the GLP-1 analog is 14 #:

or a pharmaceutically acceptable salt thereof.

26. The method of claim 21, wherein the GLP-1 analog is
15 #:

H₂N

O

OH

O

OH

H
N

O

OH

O

H
N

O

O

H
N

O

O

O

O

HN

O

H-O
H

N
H

O

NH₂

E-R-I-A-Q-E-F-I-N-W-L-I-A-G-G-P-S-S-G-A-P-P-N

N
H

S-I-Y-S-D-Y-T-F-T-G-E

H-Y-N

CH₃

H₃C

O

H
N or a pharmaceutically acceptable salt thereof.

27. The method of claim 21, wherein the GLP-1 analog is 16 #:

or a pharmaceutically acceptable salt thereof.

28. The method of claim 21, wherein the GLP-1 analog is 17 #:

or a pharmaceutically acceptable salt thereof.

29. The method of claim 21, wherein the GLP-1 analog is

18 #:

H-Y-E-G-T-F-T-S-D-Y-S-I-Y-N-E-K-I-A-A-Q-E-F-V-N-W-L-L-A-G-G-P-S-S-G-A-P-P-N-S-NH₂ or a pharmaceutically acceptable salt thereof.

30. A method of treating obesity in a subject in need thereof, the method comprising administering to the subject in need thereof a GLP-1 analog or a pharmaceutically acceptable salt thereof, wherein the GLP-1 analog has general formula (I):

(SEQ ID NO: 19)
```
R₁-X₁-X₂-Glu-Gly-Thr-Phe-Thr-Ser-Asp-X₁₀-Ser-X₁₂-

X₁₃-X₁₄-X₁₅-X₁₆-X₁₇-X₁₈-X₁₉-X₂₀-Glu-Phe-X₂₃-X₂₄-Trp-

Leu-X₂₇-X₂₈-X₂₉-X₃₀-Pro-Ser-Ser-Gly-Ala-Pro-Pro-

Pro-Ser-R₂ (I)
``` wherein:

$R_1$ is H, alkyl, acetyl, formyl, benzoyl, trifluoroacetyl, pGlu or absent;

$R_2$ is $-NH_2$, $-OH$ or absent;

$X_1$ is an amino acid residue of Tyr;

$X_2$ is an amino acid residue of Aib;

$X_{10}$ is an amino acid residue of Tyr;

$X_{12}$ is an amino acid residue of Ile;

$X_{13}$ is an amino acid residue of Tyr;

$X_{14}$ is Y1;

$X_{15}$ is selected from the group consisting of amino acid residues of Asp and Glu;

$X_{16}$ is selected from the group consisting of amino acid residues of Arg and Lys;

$X_{17}$ is an amino acid residue of Ile;

$X_{18}$ is an amino acid residue of Ala;

$X_{19}$ is an amino acid residue of Ala;

$X_{20}$ is an amino acid residue of Gln;

$X_{23}$ is selected from the group consisting of amino acid residues of Ile and Val;

$X_{24}$ is an amino acid residue of Asn;

$X_{27}$ is selected from the group consisting of amino acid residues of Ile and Leu;

$X_{28}$ is an amino acid residue of Ala;

$X_{29}$ is an amino acid residue of Gly;

$X_{30}$ is an amino acid residue of Gly;

Y1 is a Lys residue comprising a substituent on a side chain, the substituent having a structure of formula $\{[2\text{-}(2\text{-amino-ethoxy})\text{-ethoxy}]\text{-acetyl}\}_a\text{-}(y\text{-Glu})_b\text{-CO-}(CH_2)_c\text{-COOH}$;

a is an integer of 1-3;

b is 1 or 2; and c is an integer of 10-30.

31. The method of claim 30, wherein the GLP-1 analog is #:

or a pharmaceutically acceptable salt thereof.

32. The method of claim 30, wherein the GLP-1 analog is

12 #:

or a pharmaceutically acceptable salt thereof.

33. The method of claim 30, wherein the GLP-1 analog is

13 #:

or a pharmaceutically acceptable salt thereof.

34. The method of claim 30, wherein the GLP-1 analog is

14 #:

or a pharmaceutically acceptable salt thereof.

35. The method of claim 30, wherein the GLP-1 analog is

15 #:

or a pharmaceutically acceptable salt thereof.

36. The method of claim 30, wherein the GLP-1 analog is

16 #:

or a pharmaceutically acceptable salt thereof.

37. The method of claim 30, wherein the GLP-1 analog is

17 #:

or a pharmaceutically acceptable salt thereof.

38. The method of claim 30, wherein the GLP-1 analog is

18 #:

or a pharmaceutically acceptable salt thereof.

\* \* \* \* \*